(12) United States Patent
Bolling et al.

(10) Patent No.: US 7,513,863 B2
(45) Date of Patent: *Apr. 7, 2009

(54) IMPLANTABLE HEART ASSIST SYSTEM AND METHOD OF APPLYING SAME

(75) Inventors: Steven F. Bolling, Ann Arbor, MI (US); Morteza Gharib, San Marino, CA (US); Gabriel Aldea, Seattle, WA (US); Mary Lynn Gaddis, Newport Beach, CA (US); Anthony J. Viole, Foothill Ranch, CA (US)

(73) Assignee: ORQIS Medical Corporation, Lake Forest, CA (US)

( * ) Notice: Subject to any disclaimer, the term of this patent is extended or adjusted under 35 U.S.C. 154(b) by 245 days.

This patent is subject to a terminal disclaimer.

(21) Appl. No.: 10/878,591

(22) Filed: Jun. 28, 2004

(65) Prior Publication Data

US 2004/0236172 A1 Nov. 25, 2004

Related U.S. Application Data

(63) Continuation of application No. 10/289,467, filed on Nov. 6, 2002, now Pat. No. 6,889,082, which is a continuation-in-part of application No. 10/171,023, filed on Jun. 11, 2002, now Pat. No. 6,685,621, which is a continuation-in-part of application No. 10/078,260, filed on Feb. 15, 2002, now Pat. No. 6,610,004, which is a continuation-in-part of application No. 09/552,979, filed on Apr. 21, 2000, now Pat. No. 6,390,969, which is a continuation-in-part of application No. 09/470,841, filed on Dec. 23, 1999, now Pat. No. 6,387,037, which is a continuation-in-part of application No. 09/289,231, filed on Apr. 9, 1999, now Pat. No. 6,428,464, which is a continuation-in-part of application No. 09/166,005, filed on Oct. 2, 1998, now Pat. No. 6,200,260.

(60) Provisional application No. 60/061,434, filed on Oct. 9, 1997.

(51) Int. Cl.
*A61N 1/362* (2006.01)

(52) U.S. Cl. .................................................. 600/16
(58) Field of Classification Search .................. 600/16
See application file for complete search history.

(56) References Cited

U.S. PATENT DOCUMENTS 2,876,769 A 3/1959 Cordova (Continued)

FOREIGN PATENT DOCUMENTS

DE 1370546 10/1974

(Continued)

OTHER PUBLICATIONS

U.S. Appl. No. 11/418,393, which is the same as US 2006/0281962, cited above.*

(Continued)

*Primary Examiner*—Carl H Layno
*Assistant Examiner*—Brian T Gedeon
(74) *Attorney, Agent, or Firm*—Knobbe, Martens, Olson & Bear, LLP

(57) ABSTRACT

An extracardiac pumping system and method for using it supplement the circulation of blood, including the cardiac output, in a patient without any component thereof being connected to the patient's heart. A battery powered pump may be implanted subcutaneously and attached to an inflow conduit fluidly coupled to a patient's femoral artery via a subcutaneous anastomosis connection. The pump draws blood from the inflow conduit and discharges it through an outflow conduit fluidly coupled to a second peripheral artery via another subcutaneous anastomosis connection. The battery may be charged extracorporeally and the pump may be operated in either a continuous or pulsatile fashion in synchronization with the patient's heart. The conduits can be housed in a multi-lumen catheter and a reservoir may be provided which fluidly communicates with the inflow conduits. An additional feature may keep blood traveling extracorporeally within the system at or near body temperature. The system is capable of adjusting outflow from the pump to optimize the mixing of red blood cells in the aorta and thereby enhance oxygen delivery to tissues by minimizing blood cell concentration in the center of the aorta.

16 Claims, 8 Drawing Sheets

U.S. PATENT DOCUMENTS

| | | |
|---|---|---|
| 2,935,068 A | 5/1960 | Donaldson |
| 3,017,885 A | 1/1962 | Robicsek |
| 3,410,263 A | 11/1968 | McGinnis |
| 3,592,184 A | 7/1971 | Watkins et al. |
| 3,692,018 A | 9/1972 | Goetz et al. |
| 3,835,864 A | 9/1974 | Rasor et al. |
| 3,885,251 A | 5/1975 | Pedrosa |
| 3,938,530 A | 2/1976 | Santomieri |
| 3,939,820 A | 2/1976 | Grayzel |
| 3,964,479 A | 6/1976 | Boag et al. |
| 4,000,739 A | 1/1977 | Stevens |
| 4,004,299 A | 1/1977 | Runge |
| 4,034,742 A | 7/1977 | Thoma |
| 4,047,849 A | 9/1977 | Clay |
| 4,051,840 A | 10/1977 | Kantrowitz et al. |
| 4,077,394 A | 3/1978 | McCurdy |
| 4,080,958 A | 3/1978 | Bregman et al. |
| 4,134,402 A | 1/1979 | Mahurkar |
| 4,135,496 A | 1/1979 | Chazov et al. |
| 4,143,616 A | 3/1979 | Bible |
| 4,154,227 A | 5/1979 | Krause et al. |
| 4,167,046 A | 9/1979 | Portner et al. |
| 4,240,409 A | 12/1980 | Robinson et al. |
| 4,302,854 A | 12/1981 | Runge |
| 4,375,941 A | 3/1983 | Child |
| 4,384,829 A | 5/1983 | Conely et al. |
| 4,385,631 A | 5/1983 | Uthmann |
| 4,405,313 A | 9/1983 | Sisley et al. |
| 4,407,271 A | 10/1983 | Schiff |
| 4,411,655 A | 10/1983 | Schreck |
| 4,447,236 A | 5/1984 | Quinn |
| 4,457,673 A | 7/1984 | Conley et al. |
| 4,459,977 A | 7/1984 | Pizon et al. |
| 4,464,164 A | 8/1984 | Troutner et al. |
| 4,522,195 A | 6/1985 | Schiff |
| 4,540,402 A | 9/1985 | Aigner |
| 4,543,087 A | 9/1985 | Sommercorn et al. |
| 4,546,759 A | 10/1985 | Solar |
| 4,552,552 A | 11/1985 | Polaschegg et al. |
| 4,569,332 A | 2/1986 | Schiff et al. |
| 4,573,997 A | 3/1986 | Wisman et al. |
| 4,611,578 A | 9/1986 | Hiemes |
| 4,625,712 A | 12/1986 | Wampler |
| 4,666,443 A | 5/1987 | Portner |
| 4,685,446 A | 8/1987 | Choy |
| 4,688,998 A | 8/1987 | Olsen et al. |
| 4,690,134 A | 9/1987 | Snyders |
| 4,692,141 A | 9/1987 | Mahurkar |
| 4,697,574 A | 10/1987 | Karcher et al. |
| 4,719,921 A | 1/1988 | Chirife |
| 4,756,302 A | 7/1988 | Portner et al. |
| 4,759,760 A | 7/1988 | Snapp, Jr. |
| 4,771,765 A | 9/1988 | Choy et al. |
| 4,798,591 A | 1/1989 | Okada |
| 4,822,357 A | 4/1989 | Forster et al. |
| 4,838,889 A | 6/1989 | Kolff |
| 4,857,062 A | 8/1989 | Russell |
| 4,861,330 A | 8/1989 | Voss |
| 4,872,874 A | 10/1989 | Taherin |
| 4,883,462 A | 11/1989 | Williamson et al. |
| 4,895,150 A | 1/1990 | Isaacson et al. |
| 4,902,272 A | 2/1990 | Milder et al. |
| 4,902,273 A | 2/1990 | Choy et al. |
| 4,906,229 A | 3/1990 | Wampler |
| 4,908,012 A | 3/1990 | Moise et al. |
| 4,925,452 A | 5/1990 | Melinyshyn et al. |
| 4,927,407 A | 5/1990 | Dorman |
| 4,944,745 A | 7/1990 | Sogand et al. |
| 4,957,504 A | 9/1990 | Chardack |
| 4,968,293 A | 11/1990 | Nelson |
| 4,976,270 A | 12/1990 | Parl et al. |
| 4,985,014 A | 1/1991 | Orejola |
| 4,994,078 A | 2/1991 | Jarvik |
| 4,995,856 A | 2/1991 | Heindl et al. |
| 4,995,857 A | 2/1991 | Arnold |
| 4,995,865 A | 2/1991 | Gahara et al. |
| 5,011,469 A | 4/1991 | Buckberg et al. |
| 5,014,715 A | 5/1991 | Chapolini |
| 5,020,516 A | 6/1991 | Biondi et al. |
| 5,041,098 A | 8/1991 | Loiterman et al. |
| 5,059,167 A | 10/1991 | Lundquist et al. |
| 5,066,285 A | 11/1991 | Hillstead |
| 5,069,662 A | 12/1991 | Bodden |
| 5,087,247 A | 2/1992 | Horn et al. |
| 5,089,017 A | 2/1992 | Young et al. |
| 5,092,844 A | 3/1992 | Schwartz et al. |
| 5,098,370 A | 3/1992 | Rahat et al. |
| 5,114,408 A | 5/1992 | Fleischhaker et al. |
| 5,116,564 A | 5/1992 | Jansen et al. |
| 5,129,878 A | 7/1992 | Takano et al. |
| 5,129,883 A | 7/1992 | Black |
| 5,131,905 A | 7/1992 | Grooters |
| 5,133,744 A | 7/1992 | Ramos Martinez |
| 5,147,281 A | 9/1992 | Thornton et al. |
| 5,147,388 A | 9/1992 | Yamazaki |
| 5,169,378 A | 12/1992 | Figuera |
| 5,169,379 A | 12/1992 | Freed et al. |
| 5,171,207 A | 12/1992 | Whalen |
| 5,176,619 A | 1/1993 | Segalowitz |
| 5,186,713 A | 2/1993 | Raible |
| 5,211,546 A | 5/1993 | Issacson et al. |
| 5,211,659 A | 5/1993 | Strimling et al. |
| 5,250,036 A | 10/1993 | Farivar |
| 5,263,978 A | 11/1993 | Kaufman et al. |
| 5,267,940 A | 12/1993 | Moulder |
| 5,273,518 A | 12/1993 | Lee et al. |
| 5,279,551 A | 1/1994 | James |
| 5,290,227 A | 3/1994 | Pasque |
| 5,300,113 A | 4/1994 | Arpesella et al. |
| 5,308,319 A | 5/1994 | Ide et al. |
| 5,318,518 A | 6/1994 | Plechinger et al. |
| 5,332,403 A | 7/1994 | Kolff |
| 5,336,205 A | 8/1994 | Zenzen et al. |
| 5,346,458 A | 9/1994 | Affeld |
| 5,352,180 A | 10/1994 | Candelon et al. |
| 5,374,239 A | 12/1994 | Mischenko |
| 5,376,113 A | 12/1994 | Jansen et al. |
| 5,378,230 A | 1/1995 | Mahurkar |
| 5,403,291 A | 4/1995 | Abrahamson |
| 5,405,329 A | 4/1995 | Durand |
| 5,411,027 A | 5/1995 | Wiklund et al. |
| 5,413,549 A | 5/1995 | Leschinsky |
| 5,417,705 A | 5/1995 | Haber et al. |
| 5,429,584 A | 7/1995 | Chiu |
| 5,433,731 A | 7/1995 | Hoegnelid et al. |
| 5,437,601 A | 8/1995 | Runge |
| 5,449,342 A | 9/1995 | Hirose et al. |
| 5,453,076 A | 9/1995 | Kiyota et al. |
| 5,453,084 A | 9/1995 | Moses |
| 5,472,417 A | 12/1995 | Martin et al. |
| 5,486,159 A | 1/1996 | Mahurkar |
| 5,503,615 A | 4/1996 | Goldstein |
| 5,505,710 A | 4/1996 | Dorsey, III |
| 5,511,958 A | 4/1996 | Chen et al. |
| 5,514,073 A | 5/1996 | Miyata et al. |
| 5,522,800 A | 6/1996 | Crocker |
| 5,533,957 A | 7/1996 | Aldea |
| 5,533,958 A | 7/1996 | Wilk |
| 5,536,250 A | 7/1996 | Klein et al. |
| 5,542,937 A | 8/1996 | Chee et al. |
| 5,554,136 A | 9/1996 | Luther |
| 5,556,390 A | 9/1996 | Hicks |
| 5,562,595 A | 10/1996 | Neisz |
| 5,571,093 A | 11/1996 | Cruz et al. |

| | | |
|---|---|---|
| 5,584,804 A | 12/1996 | Klatz et al. |
| 5,649,911 A | 7/1997 | Terotola |
| 5,672,158 A | 9/1997 | Okada et al. |
| 5,722,930 A | 3/1998 | Larson et al. |
| 5,746,575 A | 5/1998 | Westphal et al. |
| 5,746,709 A | 5/1998 | Rom et al. |
| 5,749,855 A | 5/1998 | Reitan |
| 5,776,111 A | 7/1998 | Tesio |
| 5,785,686 A | 7/1998 | Runge |
| 5,795,326 A | 8/1998 | Siman |
| 5,801,063 A | 9/1998 | Grandis et al. |
| 5,807,311 A | 9/1998 | Palestrant |
| 5,817,046 A | 10/1998 | Glickman |
| 5,824,070 A | 10/1998 | Jarvik |
| 5,851,174 A | 12/1998 | Jarvik et al. |
| 5,868,703 A | 2/1999 | Bertolero et al. |
| 5,911,685 A | 6/1999 | Siess et al. |
| 5,928,181 A | 7/1999 | Coleman et al. |
| 5,941,813 A | 8/1999 | Sievers et al. |
| 5,947,953 A | 9/1999 | Ash et al. |
| 5,961,486 A | 10/1999 | Twardowski et al. |
| 5,964,694 A | 10/1999 | Siess et al. |
| 5,965,089 A | 10/1999 | Jarvik |
| 5,997,496 A | 12/1999 | Sekiguchi et al. |
| 6,044,845 A | 4/2000 | Lewis |
| 6,059,760 A | 5/2000 | Sandmore et al. |
| 6,068,588 A | 5/2000 | Goldowsky |
| 6,083,198 A | 7/2000 | Afzal |
| 6,085,754 A | 7/2000 | Alferness et al. |
| 6,086,527 A | 7/2000 | Talpade |
| 6,102,884 A | 8/2000 | Squitieri |
| 6,135,981 A | 10/2000 | Dyke |
| 6,136,025 A | 10/2000 | Barbut et al. |
| 6,167,765 B1 | 1/2001 | Weitzel |
| 6,180,059 B1 | 1/2001 | Divino, Jr. et al. |
| 6,183,411 B1 | 2/2001 | Mortier et al. |
| 6,190,408 B1 | 2/2001 | Melvin |
| 6,200,260 B1 | 3/2001 | Bolling |
| 6,221,103 B1 | 4/2001 | Melvin |
| 6,224,540 B1 | 5/2001 | Lederman et al. |
| 6,228,052 B1 | 5/2001 | Pohndorf |
| 6,245,045 B1 | 6/2001 | Stratienko |
| 6,287,608 B1 | 9/2001 | Levin et al. |
| 6,299,575 B1 | 10/2001 | Bolling |
| 6,508,777 B1 | 1/2002 | Macoviak et al. |
| 6,371,935 B1 | 4/2002 | Macoviak et al. |
| 6,387,037 B1 | 5/2002 | Bolling et al. |
| 6,390,969 B1 | 5/2002 | Bolling et al. |
| 6,428,464 B1 | 8/2002 | Bolling |
| 6,488,662 B2 | 12/2002 | Sirimanne |
| 6,514,226 B1* | 2/2003 | Levin et al. ............ 604/9 |
| 6,558,356 B2 | 5/2003 | Barbut |
| 6,592,567 B1* | 7/2003 | Levin et al. ............ 604/509 |
| 6,610,004 B2 | 8/2003 | Viole et al. |
| 6,685,621 B2 | 2/2004 | Bolling et al. |
| 6,719,749 B1 | 4/2004 | Schweikert et al. |
| 6,749,598 B1 | 6/2004 | Keren et al. |
| 6,770,049 B2 | 8/2004 | Ludt et al. |
| 7,125,376 B2 | 10/2006 | Viole et al. |
| 7,331,921 B2 | 2/2008 | Viole et al. |
| 2002/0111577 A1 | 8/2002 | Sirimanne et al. |
| 2002/0161322 A1 | 10/2002 | Utterberg et al. |
| 2002/0169413 A1 | 11/2002 | Keren et al. |
| 2002/0188166 A1 | 12/2002 | Viole et al. |
| 2002/0188167 A1 | 12/2002 | Viole et al. |
| 2003/0069468 A1 | 4/2003 | Bolling |
| 2003/0083617 A1 | 5/2003 | St. Germain et al. |
| 2003/0144628 A1 | 7/2003 | Sirimanne |
| 2003/0187367 A1 | 10/2003 | Odland |
| 2004/0019251 A1 | 1/2004 | Viole et al. |
| 2004/0236173 A1 | 11/2004 | Bolling et al. |
| 2005/0085683 A1 | 4/2005 | Bolling et al. |
| 2006/0264695 A1 | 11/2006 | Viole et al. |
| 2006/0270894 A1 | 11/2006 | Viole et al. |
| 2006/0281962 A1* | 12/2006 | Bolling et al. ............ 600/16 |

FOREIGN PATENT DOCUMENTS

| | | |
|---|---|---|
| DE | 91 11 200 U | 11/1991 |
| EP | 0232074 | 1/1987 |
| EP | 0 411 605 A1 | 1/1990 |
| EP | 0 405 749 A1 | 5/1990 |
| EP | 0 533 432 A1 | 3/1993 |
| EP | 0 711 574 A1 | 5/1996 |
| FR | 2201908 | 5/1974 |
| GB | 2 174 151 A | 1/1985 |
| JP | S63-55943 | 11/1988 |
| JP | H02-286170 | 11/1990 |
| JP | 08257001 A | 10/1996 |
| RU | 1303165 A2 | 1/1985 |
| WO | WO 86/01416 | 3/1986 |
| WO | WO 94/05347 | 3/1994 |
| WO | WO 96-17644 | 6/1996 |
| WO | WO 96/18358 | 6/1996 |
| WO | WO 98/14225 | 3/1997 |
| WO | WO 97/15228 | 5/1997 |
| WO | WO 98/34676 | 8/1998 |
| WO | WO 99/16498 | 4/1999 |
| WO | WO 99/19010 | 4/1999 |
| WO | WO 99/21605 | 5/1999 |
| WO | WO 99/42156 | 8/1999 |
| WO | WO 99/59652 | 11/1999 |
| WO | WO 00-04943 | 2/2000 |
| WO | WO 00/41612 | 7/2000 |
| WO | WO 00/61207 | 10/2000 |
| WO | WO 01-32256 | 5/2001 |
| WO | WO 01/74419 A1 | 10/2001 |
| WO | WO 02/064204 | 8/2002 |
| WO | WO 02/070039 A2 | 9/2002 |
| WO | WO 03/070299 A1 | 8/2003 |

OTHER PUBLICATIONS

PCT International Search Report, App. No. PCT/US 01/42774, App. Date: Oct. 15, 2001, 6 Pages.
PCT International Search Report, App. Date: Jun. 18, 2003, PCT/US/03/04401.
JAMA, Jan. 8, 1968, vol. 203, No. 2, Initial Clinical Experience with Intra-aortic Balloon Pumping in Cardiogenic Shock. pp. 113-118.
Article: A Mechanical Auxiliar Ventricle. pp. M340-344.
Article: Effect of Stationary Guiding Vanes on Improvement of the Washout Behind the Rotor in Centrifungal Blood Pumps: pp. M220-M224.
Article: An Implantable Seal-less Centrifugal Pump: Comparison of Ultrasonic Transit Time and Ultrasonic Doppler Systems: pp. 808-815.
Article: O.H. Frazier, MD. Long-Term Ventricular Support with the Heartmate in Patients Undergoing Bridge-to-Transplant Operation: 3PP total.
Article: Concepts in the Application of Pneumatic Ventricular Assist Devices for Ischemic Myocardial Injury. pp. 162-168.
Article: Long-Term Left Ventricular Assist Device Use Before Transplantation: pp. M530-M534.
Article: In Vitro Characterization of a Magnetically Suspended Continuous Flow Ventricular Assist Device: pp. M359-M360.
Article: Estimation of Left Ventricular Function in Patients With a Left Ventricular Assist device: M544-M551.
Article: Mechanical Auxiliary Ventricle. pp. M345-M344.
Article: Long Term Follow Up of Survivors of Postcardiotomy Circulatory Support. Ruzevich et al.; 4535, A.S.A.I.O. Transactions 34 (1988) April-June, No. 2, Hagerstown, MD, USA. pp. 16-124.

Article: Mechanical Cardiopulmonary Support During Arteriography and Surgical Correction of Coronary Insufficiency Producing Myocardial Infarction with Cardiogenic Shock: Carlson et al. Journal of the Association for the Advancment of Medical Instrumentation. vol. 6, No. 3. May-Jun. 1972; pp. 244-248.
Article: The Sternotomy Hemopump, A Second Generation Intraarterial Assist Device. pp. M218-M220, 223.
Article: Transarterial Closed-Chest Left Ventricular (TaCLV) Bypass. pp. 386-390.
Article: First Clinical Application of transarterial Closed-Chest Left Ventricular (TaCLV) Bypass. pp. 386-391.
Article: Implantable Left Ventricular Assist Device. pp. 1522-1533.
Article: Effects of Partial and Complete Unloading of The Failing Left Ventricle by Transarterial Left Heart Bypass. pp. 865-872.
Article: Hydrodynamic Properties of a New Percutaneous Intra-aortic Axial Flow Pump. Reitan et al. ASAIO Journal 2000. pp. 323-328.
Article: Hemodynamic Effects of the Concomitant Use of Intra-Aortic Balloon Pumping and Venoarterial Bypass without Oxygenation in Cardigenic Shock. Takamoto et al. Intra-Aortic Pumping & Ventroaterial Bypass. vol. 19. No. 6. Nov. 1978. pp. 938-945.
Journal of the Association for the Advancement of Medical Instrumentation, vol. 10, No. 5, Sep.-Oct. 1976, p. 215; Medical Instrumentation Editorial.
Dormandy, Goetz, and Kripke; Surgery, Feb. 1969, vol. 65, No. 2, pp. 311-320; Hemodynamics and coronary blood flow with counterpulsation.
The New England Journal of Medicine, Article: Treatment of Severe Fluid Overload by Ultrafiltration, vol. 291, No. 15, Oct. 10, 1974, pp. 747-751.
Magnetically Suspended Vad. pp. M361. 363, 364.
Magovern, George J. Jr, M.D.; Use of Biomedics Pump in Postoperative Circulatory Support: 6PP total.
Shook, Bruce J., MS Eng.; The Abiomed BVS 5000 Biventricular Support System. 6 PP total.
Jeavanandan, Valluvan, M.D. et al.; TCI Heartmate Left Ventricular Assist System: Results with Bridge to Transplant and Chronic Support: 5 PP total.
Ramasamy, Narayanan, PhD et al.; Novacor LVAS: Results with Bridge Transplant to Chronic Support: 3 PP Total.
Emery, Robert M. M.D., et al; Uses of Mechanical Circulatory Assist Devices at Minneapolis Heart Institute: 5PP total.
McBride, Lawerence R., M.D., et al.; Anticoagulation in Patients with Ventricular Assist Devices: 1 Pg.
Pifarre, Roque, M.D. et al.; Bridge to Transplantation with the total Articical heart: The Loyal Experience 5 PP total.
Khanwiljkar, Pratap S., MS, MBA, et al.; Future Prospects for a totally Implantable Artificial Heart: 8 pp total.
Birtwell, W. et al. The evolution of counterpulsation techniques. Med Instrum 1976; 10(5): 217-23.
Blythe, D. Percutaneous axillary artery insertion of an intra-aortic balloon pump. Annesth and Intensive Care 1995; 23(3): 406-7.
Bonchek, L. et al. Direct Ascending Aortic Insertion of the "Percutaneous" Intraaortic Balloon Catheter in the Open Chest: Advantages and Precautions. Ann Thorac Surg 1981; 32(5): 512-14.
Clark, R. E. et al. Future devices and directions. Progress in Cardiovascular Diseases, 43(1) Jul./Aug. 2000: 95-100.

Cochran, R. et al. Ambulatory Intraaortic Balloon Pump Use as Bridge to Heart Transplant. Ann Thorac Surg 2002; 74: 746-52.
Cook, L. et al. Intra-aortic balloon pump complications: a five-year retrospective study of 283 patients. Heart & Lung 1999; 28(3): 195-202.
Crystal, E. et al. Incidence and Clinical Significance of Bacteremia and Sepsis Among Cardiac Patient Treated with Intra-Aortic Balloon Counterpulsation Pump. Amer J Cardiol 2000; 86: 1281-1284.
Dembitsky, W. Bridging from acute to chronic devices. Ann Thorac Surg 1999; 68: 724-28.
Goldstein, A. H. et al. Development of an Implantable Centrifugal Blood Pump. ASAIO 1992; 38(3): M362-5.
Goldstein, A. H. et al. Predictable Reduction in Left Ventricular Stroke Work and Oxygen Utilization With an Implantable Centrifugal Pump. Ann Thorac Surg 1994; 58 (4): 1018-24.
Jaski, B. et al. Anterograde Perfusion in Acute Limb Ischemia Secondary to Vascular Occlusive Cardiopulmonary Support. Cath and Cardiovasc Diag 1995; 35: 373-76.
Magovern, G. Nonpulsatile Circulatory Support: Techniques of Insertion. Ann Thorac Surg 1993; 55: 266-72.
McBride, L. et al. Axillary Artery Insertion of an Intraaortic Balloon Pump. Ann Thorac Surg 1989; 48: 874-5.
Nishimura et al. The enabler cannula pump: a novel circulatory support system. The International Journal of Artificial Organs, vol. 22, No. 5, 1999, pp. 317-323.
Sharony et al. Cardiopulmonary Support and Physiology-The Intra-Aortic Cannula Pump: A Novel Assist Device for the Acutely Failing Heart. The Journal of Thoracic and Cardiovascular Surgery, Nov. 1992, vol. 118, No. 5, pp. 924-929.
Sharony, R. et al. Right heart support during off-pump coronary artery surgert—a multi-center study. Heart Surg Forum. 2002; 5(1): 13-6.
Takagaki et al. A Novel Miniature Ventricular Assist Device for Hemodynamic Support. ASAIO Journal 2001, pp. 412-416.
PCT International Search Report, App. No. PCT/US2003/004853, Mar. 7, 2003.
PCT International Preliminary Examination Report, App. No. PCT/US2003/004853, Jul. 26, 2004.
EPO Office Action, App. No. 03711112.7, Nov. 9, 2006.
PCT International Search Report, App. No. PCT/US2004/033575, Feb. 18, 2005.
PCT Written Opinion of the International Searching Authority, App. No. PCT/US2004/033575, Feb. 16, 2006.
PCT International Preliminary Report on Patentability, App. No. PCT/US2004/033575, Apr. 18, 2006.
PCT International Search Report, App. No. PCT/US2000/006749, Jun. 27, 2000.
PCT Written Opinion, App. No. PCT/US2000/006749, Jan. 18, 2001.
PCT International Preliminary Examination Report, App. No. PCT/US2000/006749, Jul. 23, 2001.
EPO Office Action, App. No. 00917948.2, Mar. 26, 2003.
EPO Office Action, App. No. 00917948.2, Dec. 19, 2003.
Aranki, S. et al. Femoral Veno-Arterial Extracorporeal Life Support With Minimal or No Heparin. Ann Thorac Surg 1993; 56: 149-155.
Champsaur, G. et al. Use of the Abiomed BVS System 5000 as a bridge to cardiac transplantation. J Thorac Cardiovasc Surg 1990; 100: 122-128.

Clark, R. E. et al., Left Ventricular Support With the Implantable AB-180 Centrifugal Pump in Sheep With Acute Myocradial Infraction. ASAIO 1998; 44(6): 804-811.

Clark, R. E. et al., Small, Low-Cost Implantable Centrifugal Pump for Short-Term Circulatory Assistance. Ann Thorac Surg 1996; 61: 452-456.

Clark, R. E., Progress in the Clinical Application of the AB-180 Circulatory Support System. Journal of Circulatory Support (1998) vol. 1, No. 1, 21-26.

Griffin, W. P. et al. AB-180 Circulatory Support System: Summary of Development and Phase I Clinical Trial. ASAIO 1998; 44(5): M719-724.

Ide, Hirofumi et al., Hemodynamic Evaluation of a New Left Ventricular Assist Device, Artifical Organs 16 (3): 286-290; 1992.

Ide, Hirofumi et al., Evaluation of the Pulsatility of a New Pulsatile Left Ventricular Assist Device--the Integrated Cardioassist Catheter--in Dogs, J. of Thoracic and Cardiovascular Surgery 107 (2): 569-575; Feb. 1994.

Kantrowitz, Adrian, et al,; A Mechanical Auxiliary Ventricle, Histologic Responses to Long-Term, Intermittent Pumping in Calves, ASAIO Journal 1995;41: M340-M345.

Konertz, W. et al. Clinical Experience With the MEDOS HIA-VAD System in Infants and Children: A Preliminary Report. Ann Thorac Surg 1997; 63: 1138-1144.

Magovern, J. A. et al. Clinical Results With the AB-180 Left Ventricular Assist Device. Ann Thorac Surg 2001; 71: S121-124.

Martin, J. et al. MEDOS HIA-VAD Biventricular Assist Device for Bridge to Recovery in Fulminant Myocarditis. Ann Thorac Surg 1997; 1145-1146.

Mihaylov, D. et al., Evaluation of the Optimal Driving Mode During Left Ventricular Assist with Pulsatile Catheter Pump in Calves, Artificial Organs 23(12): 1117-1122; 1999.

Mihaylov, Dimiter et al., Development of a New Introduction Technique for the Pulsatile Catheter Pump, Artificial Organs 21(5): 425-427; 1997.

Murakami, Taiji et al., In Vitro and in Vitro Testing of an Implantable Motor Driven Left Ventricular Device, Artificial Organs 20(2): 152-155; 1996.

Morsink, PLJ et al., Numerical Modeling of Blood Flow Behaviour in the Valved Catheter of the PUCA Pump, a LVAD, The International Journal of Artificial Organs 20(5): 277-284; 1997.

Pacella, J. J. et al. Modified Fabrication Techniques Lead to Improved Centrifugal Blood Pump Performance. ASAIO 1994; 40: M767-M772.

Rakhorst, Gerhard et al., In Vitro Evaluation of the Influence of Pulsatile Intraventricular Pumping on Ventricular Pressure Patterns, Artificial Organs 18(7): 494-499; 1994.

Reddy, R. C. et al. End Organ Function With Prolonged Nonpulsatile Circulatory Support. ASAIO 1995; 41: M547-M551.

Reedy, J. et al. Mechanical Cardiopulmonary Support for Refractory Cardiogenic Shock. Heart & Lung 1990; 19(5): 514-523.

Savage, E. B. et al. The AB-180 Circulatory Support System: Summary of Development and Plans for Phase I Clinical Trial. Ann Thorac Surg 1999; 68: 768-774.

Schima, Heinrich, et al., An Implantable Seal-less Centrifugal Pump with Integrated Double-Disk Motor; Artificial Organs, 19(7):639-643.

Schima, Heinrich, et al., Flow Measurement at the Pump Head of Centrifugal Pumps: Comparison of Ultrasonic Transit Time and Ultrasonic Doppler Systems; Artificial Organs, 21(7):808-815.

Verkerke, Gijsbertus et al., Numerical Simulation of the Pulsating Catheter Pump: A Left Ventricular Assist Device, Artificial Organs 23(10): 924-931; 1999.

Verkerke, Bart et al., The PUCA Pump: A Left Ventricular Assist Device, Artificial Organs 17(5): 365-368; 1993. cited by other.

Verkerke, CJ et al., Numerical Simulation of the PUCA Pump, A Left Ventricular Assist Device, Abstracts of the XIXth ESAO Congress, The International Journal of Artificial Organs 15(9): 543; 1992.

Wenger, R., et al. Flow Dynamics of Peripheral Venous Catheters During Extracorporeal Membrane Oxygenation With a Centrifugal Pump. J Thora Cardiovasc Surg 1988; 96:478-484.

Westaby, S. et al. Mechanical Bridge to Recovery in Fulminant Myocarditis. Ann Thorac Surg 2000; 70: 278-282.

* cited by examiner

IMPLANTABLE HEART ASSIST SYSTEM AND METHOD OF APPLYING SAME

RELATED APPLICATIONS

This application is a continuation of U.S. application Ser. No. 10/289,467, filed Nov. 6, 2002, now U.S. Pat. No. 6,889,082, which is a continuation-in-part of U.S. application Ser. No. 10/171,023, filed on Jun 11, 2002, now U.S. Pat. No. 6,685,621, which is a continuation-in-part of U.S. application Ser. No. 10/078,260, filed on Feb 15, 2002, now U.S. Pat. No. 6,610,004, which is a continuation-in-part of U.S. application Ser. No. 09/552,979, filed on Apr. 21, 2000, now U.S. Pat. No. 6,390,969 B1, which is a continuation-in-part of U.S. application Ser. No. 09/470,841, filed on Dec. 23, 1999, now U.S. Pat. No. 6,387,037 B1, which is a continuation-in-part of U.S. application Ser. No. 09/289,231, filed on Apr. 9, 1999, now U.S. Pat. No. 6,428,464 B1, which is continuation-in-part of U.S. application Ser. No. 09/165,005, filed on Oct. 2, 1998, now U.S. Pat. No. 6,200,260 B1, which claims the benefit of U.S. Provisional Application Ser. No. 60/061,434, filed Oct. 9, 1997.

BACKGROUND OF THE INVENTION

1. Field of the Invention

The present invention relates generally to a system for assisting the heart and, in particular, to an extracardiac pumping system and a method for both supplementing the circulation of blood through the patient and for enhancing vascular blood mixing using a minimally invasive procedure.

2. Description of the Related Art

During the last decade, congestive heart failure (CHF) has burgeoned into the most important public health problem in cardiovascular medicine. As reported in Gilum, R. F., Epidemiology of Heart Failure in the U S., 126 Am. Heart J. 1042 (1993), four hundred thousand (400,000) new cases of CHF are diagnosed in the United States annually. The disorder is said to affect nearly 5 million people in this country and close to 20 million people worldwide. The number of hospitalizations for CHF has increased more than three fold in the last 15 years. Unfortunately, nearly 250,000 patients die of heart failure annually. According to the Framingham Heart Study, the 5-year mortality rate for patients with congestive heart failure was 75 percent in men and 62 per cent in women (Ho, K. K. L., Anderson, K. M., Kannel, W. B., et al., Survival After the Onset of Congestive Heart Failure in Framingham Heart Study Subject, 88 Circulation 107 (1993)). This disorder represents the most common discharge diagnosis for patients over 65 years of age. Although, the incidence of most cardiovascular disorders has decreased over the past 10 to 20 years, the incidence and prevalence of congestive heart failure has increased at a dramatic rate. This number will increase as patients who would normally die of an acute myocardial infarction (heart attack) survive, and as the population ages.

CHF manifests itself primarily by exertional dyspnea (difficult or labored breathing) and fatigue. Three paradigms are used to describe the causes and therapy of CHF. The first views this condition in terms of altered pump function and abnormal circulatory dynamics. Other models describe it largely in terms of altered myocardial cellular performance or of altered gene expression in the cells of the atrophied heart. In its broadest sense, CHF can be defined as the inability of the heart to pump blood throughout the body at the rate needed to maintain adequate blood flow, and many of the normal functions of the body.

To address CHF, many types of cardiac assist devices have been developed. A cardiac or circulatory assist device is one that aids the failing heart by increasing its pumping function or by allowing it a certain amount of rest to recover its pumping function. Because congestive heart failure may be chronic or acute, different categories of heart assist devices exist. Short of a heart transplant, at least two types of chronic heart assist systems have been developed. One type employs a full or partial prosthetic connected between the heart and the aorta, one example of which is commonly referred to as a LVAD—Left Ventricular Assist Device. With reference to FIG. 1 herein, one example of a LVAD 2 is shown. The LVAD comprises a pump and associated valves 4 that draws blood directly from the apex of the left ventricle 6 and directs the blood to the aortic arch 8, bypassing the aortic valve. In this application, the left ventricle stops functioning and does not contract or expand. The left ventricle becomes, in effect, an extension of the left atrium, with the LVAD 2 taking over for the left ventricle. The ventricle, thus, becomes a low-pressure chamber. Because the intent is to take over for the left ventricle, the LVAD operates by pumping blood at cardiac rates. With an LVAD, oxygenated blood circulation is established sufficient to satisfy the demand of the patient's organs. Under these circumstances, however, continuous flow may not be desired because the patient's arterial system is deprived of pulsatile wave flow, which is beneficial to certain parts of the patient.

Another type of chronic heart assist system is shown in U.S. Pat. No. 5,267,940 to Moulder. Moulder describes a pump implanted into the proximal descending aorta to assist in the circulation of blood through the aorta. Because it is intended to pump blood flowing directly out of the heart, it is important that the Moulder device operate in a properly timed, pulsatile fashion. If it is not operated in direct synchronization with the patient's heart, there is a risk that the pump might cause "carotid steal phenomenon" where blood is drawn away from the patient's brain through the carotid arteries when there is insufficient blood in the left ventricle.

In addressing acute CHF, two types of heart assist devices have been used. One is counterpulsatory in nature and is exemplified by an intra-aortic balloon pump (IABP). With an IABP, the balloon is collapsed during isovolumic contraction, providing a reduced pressure against which the heart must pump blood, thereby reducing the load on the heart during systole. The balloon is then expanded, forcing blood omnidirectionally through the arterial system. Another example of this first type employs one or more collapsible chambers in which blood flows passively into the chamber during systole, as is shown in U.S. Pat. No. 4,240,409 to Robinson et al. The chamber is then collapsed and the blood forcibly returned to the aorta. These devices simulate a chamber of the heart and depend upon an inflatable bladder to effectuate pumping action, requiring an external pneumatic driver. Moreover, they do not operate as a continuous flow system, operating exclusively in pulsatile fashion.

A second type of acute assist device utilizes an extracorporeal pump, such as the Biomedicus centrifugal pump, to direct blood through the patient while surgery is performed on the heart. In one example, described in U.S. Pat. No. 4,968,293 to Nelson, the heart assist system employs a centrifugal pump in which the muscle of the patient is utilized to add pulsatility to the blood flow. The Nelson device is used to bypass a portion of the descending aorta.

Another device, shown in U.S. Pat. No. 4,080,958 to Bregman et al., utilizes an inflatable and collapsible bladder to assist in blood perfusion during heart trauma and is intended to supplement a conventional heart-lung machine by imparting pulsatile actuation. In the primary embodiment disclosed in Bregman, the balloon is controlled to maintain sufficient pressure at the aortic root during diastole to ensure sufficient blood perfusion to the coronary arteries. In an alternative embodiment, a low resistance outlet from the aorta to the inferior vena cava is provided to reduce the aortic pressure during systole, thus, reducing the hemodynamic load on the left ventricle.

Other devices, such as that shown in U.S. Pat. No. 4,034,742 to Thoma, depend upon interaction and coordination with a mechanical pumping chamber containing a movable pumping diaphragm. These devices are intended primarily for application proximate the heart and within the patient's thorax, requiring major invasive surgery.

Many CHF devices are acutely used in the perioperative period. For example, U.S. Pat. No. 4,995,857 to Arnold discloses a perioperative device to pump blood at essentially cardiac rates during surgery when the heart has failed or has been stopped to perform cardiac surgery. The Arnold system temporarily replaces the patient's heart and lung and pumps blood at cardiac rates, typically 5 to 6 liters/min. Like all systems that bypass the heart and the lungs, an oxygenator is required. Of course, with any system that includes an oxygenator, such as the conventional heart-lung machine, the patient cannot be ambulatory.

With early IABP devices, a polyurethane balloon was mounted on a vascular catheter, inserted into the femoral artery, and positioned in the descending aorta just distal to the left subclavian artery. The balloon catheter was connected to a pump console that pumped helium or carbon dioxide into the balloon during diastole to inflate it. During isovolumic contraction, i. e., during the brief time that the aortic valve is closed and the left ventricle continues to contract, the gas used to actuate the balloon was rapidly withdrawn to deflate the balloon. This reduced the pressure at the aortic root when the aortic valve opened. In contrast, during diastole, the balloon was inflated, causing the diastolic pressure to rise and pushing the blood in the aorta distally towards the lower part of the body (on one side of the balloon) and proximally toward the heart and into the coronary arteries (on the other).

The major advantage in such a counterpulsation device was systolic deflation, which lowered the intra-aortic volume and pressure, reducing both afterload and myocardial oxygen consumption. In other words, when the balloon is inflated, it creates an artificially higher pressure in the aorta, which has the ancillary benefit of greater perfusion through the coronary arteries. When the balloon deflates, just before the aortic valve opens, the pressure and volume of the aorta decrease, relieving some of the hemodynamic burden on the heart. These physiologic responses improved the patient's cardiac output and coronary circulation, temporarily improving hemodynamics. In general, counterpulsation with an IABP can augment cardiac output by about 15%, this being frequently sufficient to stabilize the patient's hemodynamic status, which might otherwise rapidly deteriorate. When there is evidence of more efficient pumping ability by the heart, and the patient has moved to an improved class of hemodynamic status, counterpulsation can be discontinued, by slowly weaning while monitoring for deterioration.

Until 1979, all IABP catheters were inserted via surgical cutdown, generally of the femoral artery. Since then, the development of a percutaneous IABP catheter has allowed quicker, and perhaps safer, insertion and has resulted in more expeditious institution of therapy and expansion of clinical applications. Inflation and deflation of the balloon, however, requires a pneumatic pump that is sufficiently large that it must be employed extracorporeally, thereby restricting the patient's movements and ability to carry out normal, daily activities. IABP devices are, thus, limited to short term use, on the order of a few days to a few weeks.

As discussed above, a variety of ventricular assist pumping mechanisms have been designed. Typically associated with LVADs are valves that are used in the inlet and outlet conduits to insure unidirectional blood flow. Given the close proximity of the heart, unidirectional flow was necessary to avoid inadvertent backflow into the heart. The use of such valves also minimized the thrombogenic potential of the LVAD device.

Typically, the pump associated with older LVADs was a bulky pulsatile flow pump, of the pusher plate or diaphragm style, such as those manufactured by Baxter Novacor or TCI, respectively. Given that the pump was implanted within the chest and/or abdominal cavity, major invasive surgery was required. The pumps were typically driven through a percutaneous driveline by a portable external console that monitors and reprograms functions.

Alternatively, rotary pumps, such as centrifugal or axial pumps, have been used in heart assist systems. With centrifugal pumps, the blood enters and exits the pump practically in the same plane. An axial pump, in contrast, directs the blood along the axis of rotation of the rotor. Inspired by the Archimedes screw, one design of an axial pump has been miniaturized to about the size of a pencil eraser, although other designs are larger. Despite its small size, an axial pump may be sufficiently powerful to produce flows that approach those used with older LVADs. Even with miniaturized pumps, however, the pump is typically introduced into the left ventricle through the aortic valve or through the apex of the heart, and its function must be controlled from a console outside the body through percutaneous lines.

All of these heart assist systems referred to above serve one or both of two objectives: (1) to improve the performance of a patient's operative-but-diseased heart from the minimum, classified as NYHAC Class IV, to practically normal, classified as I or 0; or (2) to supplement oxygenated blood circulation through the patient to satisfy organ demand when the patient's heart is suffering from CHF. With such systems, extreme pumping and large amounts of energy, volume, and heat dissipation are required.

Many of these heart assist systems have several general features in common: 1) the devices are cardiac in nature; i. e., they are placed directly within or adjacent to the heart, or within one of the primary vessels associated with the heart (aorta), and are often attached to the heart and/or aorta; 2) the devices attempt to reproduce pulsatile blood flow naturally found in the mammalian circulatory system and, therefore, require valves to prevent backflow; 3) the devices are driven from external consoles, often triggered by the electrocardiogram of the patient; and 4) the size of the blood pump, including its associated connectors and accessories, is generally unmanageable within the anatomy and physiology of the recipient. Due to having one or more of these features, the prior art heart assist devices are limited in their effectiveness and/or practicality.

Many of the above identified prior art systems, generally referred to as Mechanical Circulatory Assist Devices, are not the only means, however, used to treat patients with congestive heart failure (CHF). Most CHF patients are prescribed as many as five to seven different drugs to ameliorate their signs and symptoms. These drugs may include diuretics, angiotensin converting enzyme (ACE) inhibitors, beta-blockers, cardiac glycosides, and peripheral vasodilators. The rationale for pharmacological intervention in heart failure include minimizing the load on the heart, improving the pumping action of the heart by enhancing the contractility of the muscle fibers, and suppression of harmful neurohormonal compensatory mechanisms that are activated because of the decreased pumping function of the heart.

Noncompliance with what is often a complex drug regime may dramatically adversely affect the recovery of a CHF patient leading to the need for hospitalization and possibly morbidity and mortality. In addition, ACE inhibitors and diurectics can cause hypotension, which leads to decreased organ perfusion or an increasing demand on the heart to pump more blood. This leads to an inability, in many cases, to prescribe the most effective dosage of ACE inhibitors and a less than optimum outcome for the patient. Patients suffering from CHF with the underlying cause of mitral valve insufficiency have been able to have their diuretics reduced following surgical repair of their mitral valve. This is due to an increased cardiac output and arterial pressures (as a result of the correction of the problem) resulting in more effective organ perfusion. With the reduction in the use of diuretics and the resultant hypotension, more effective dosages of ACE inhibitors can be used with more favorable outcomes. In addition, it is easier for the patient to follow a less complex drug regime, eliminating the costly and life threatening risks associated with noncompliance.

When blood flow through the coronary arteries falls below the level needed to provide the energy necessary to maintain myocardial function, due often to a blockage in the coronary arteries, a myocardial infarction or heart attack occurs. This is a result of the blockage in the coronary arteries preventing blood from delivering oxygen to tissues downstream of the blockage. The closer the blockage is to the coronary ostia, however, the more severe and life threatening the myocardial infarction. The farther the location of the blockage is from the coronary ostia, the smaller the area of tissue or myocardium that is at risk. As the energy stored in the affected area decreases, myocardial cells begin to die. The larger the area that dies due to the loss of oxygen, the more devastating the infarction. To reduce the area at risk, at least two known options are to either increase the oxygen supply to the affected area or decrease the energy demands of the heart to prolong energy stores until the blockage can be removed or reduced. One particular method to increase blood flow, thereby increasing delivery of oxygen to the affected area, is through a technique called retroperfusion. This is accomplished by passing a cannula into either the right or left ventricle (depending on the area of the blockage) and perfusing oxygenated blood retrograde up the coronary artery on the downstream side of the blockage. Another method is to use drugs to increase the force of contraction of the myocardium, creating increased blood flow across the blocked area. Yet another method is to use drugs, such as pentoxifylline, aspirin, or TPA (tissue plaminogen activator), to reduce the viscosity of (thin out) the blood, inhibit platelet aggregation, or lyse thrombi (clots), respectively, thus, allowing more blood to pass by the blockage. The goal of all of these methods is to increase the delivery of oxygen to the tissue at risk.

The alternative option mentioned above is to reduce the energy demands of the myocardium and increase the amount of time before irreversible damage occurs. This can be accomplished by reducing the workload of the left ventricle (which is the largest energy-consuming portion of the heart). An IABP is placed into the aorta and used as described above, resulting in a decreased afterload on the heart and increased perfusion of the coronary arteries and peripheral organs. An alternative way to reduce myocardial oxygen demand is to reduce the volume of blood the left ventricle must pump. This can be accomplished by reducing the load on the left ventricle, such as in a cardiopulmonary bypass or use of an LVAD. Unloading the left ventricle decreases the energy requirements of the myocardium and increases the amount of time before irreversible damage occurs. This provides an opportunity to more effectively remove or decrease the blockage and salvage myocardial function. To be successful, each of these techniques must be implemented within a short amount of time after the onset of a myocardial infarction. The disadvantage, however, is that each of these techniques can only be performed in an emergency room or hospital setting. Unless the patient is already in the hospital when the myocardial infarction occurs, there is usually some level of irreversible damage and subsequent loss of myocardial function.

It would be advantageous, therefore, to employ a heart assist system that avoids major invasive surgery and also avoids the use of peripheral equipment that severely restricts a patient's movement. It would also be advantageous to have such a heart assist system that can be employed in a non-hospital setting for ease of treating acute heart problems under emergency conditions.

SUMMARY OF THE INVENTION

The object of the present invention is to address the aspect of CHF that results from altered pump function and abnormal circulatory dynamics while overcoming the limitations of prior art heart assist systems. Without functioning as a bypass to one or more of a patient's organs, the present invention comprises an extracardiac pumping system for supplementing the circulation of blood through the patient without any component thereof being connected to the patient's heart or primary vessels. Thus, it is extracardiac in nature. With the ability to be applied within a minimally invasive procedure, the present invention significantly improves the condition of the patient suffering from CHF, resulting in the patient feeling much better, even where CHF continues. By supplementing the pumping action of the heart, in lieu of replacing it, the present system takes advantage of the pulsatile action of the heart, despite its weakened condition, to effectively deliver blood to body organs that benefit from pulsatile delivery of oxygenated blood. As a result, the present system is capable of being operated in a continuous flow fashion or, if desired, in a pulsatile flow fashion.

An ancillary but important benefit of the present invention is the ability to apply the present invention in such a way as to also reduce the pumping load on the heart, thereby potentially permitting the heart to recover during use. With the present invention, no bulky pump, valves or oxygenator are required, and no thoracic invasion with major cardiac surgery is required. Indeed, a significant advantage of the present invention is its simplicity while achieving extraordinary results in improving the condition of a patient suffering from CHF.

The extracardiac system of the present invention preferably comprises, in one example, a rotary pump configured to pump blood through the patient at subcardiac rates; i. e., at a flow rate significantly below that of the patient's heart. Other types of pumps or flow generating mechanisms may be effective as well. Pumping the blood tends to revitalize the blood to a certain extent by imparting kinetic and potential energy to the blood discharged from the pump. Importantly, the preferred pump for the present invention pumping system is one that requires a relatively low amount of energy input, when compared to prior art pumps designed to pump at cardiac rates. The pump may be implanted or not, depending upon the capability, practicality, or need of the patient to be ambulatory.

The present system also comprises an inflow conduit fluidly coupled to the pump, to direct blood to the pump from a first peripheral blood vessel, and an outflow conduit fluidly coupled to the pump, to direct blood from the pump to a second peripheral blood vessel. The connection of the inflow and outflow conduits to the respective blood vessels is performed subcutaneously; not so deep as to involve major invasive surgery. In other words, minimally subdermal. This permits application of the connections in a minimally-invasive procedure. Preferably, the connections to the blood vessels are just below the skin or just below the first layer of muscle, depending upon the blood vessels at issue or the location of the connection, although slightly deeper penetrations may be necessary for some patients or for some applications.

In an alternative embodiment, the present system is applied at a single cannulated site using, for example, a multi-lumen catheter having at least one lumen as an inflow lumen and a second lumen as an outlet lumen. The multi-lumen catheter has an inflow port in fluid communicating with the inflow lumen. With this embodiment, blood is drawn into the inflow port of the first lumen from a first peripheral blood vessel site, preferably the blood vessel into which the multi-lumen catheter is inserted. The output of the pump directs blood through a second (outlet) port at the distal end of the second lumen that is preferably located in a second peripheral vessel site. This method accomplishes the same beneficial results achieved in the previously described embodiments, but requires only a single cannulated site, rather than two such sites. It should be appreciated that the multi-lumen catheter could be used in a manner where the outflow of the cannula is to the first peripheral site, while the inflow is drawn from the second peripheral vessel. Further still, it should be appreciated that the inflow could be positioned to draw blood from a peripheral vessel at the site of entry into the patient while the outflow could be positioned in the aorta, proximate an arterial branch.

In one embodiment of the extracardiac system, the pump is a continuous flow pump, a pulsatile pump, and/or a pump that is configured to generate flow in both a continuous and pulsatile format. The pump may be implantable and is used to connect two peripheral arteries, such as the femoral artery at the inflow and the left axillary artery at the outflow, although other peripheral blood vessels are contemplated, including other arteries and/or veins, as well as any singular and/or cumulative combination thereof. An alternative embodiment employs both a continuous flow and a pulsatile flow pump connected in parallel or in series and operating simultaneously or in an alternating fashion. Yet another alternative embodiment employs a rotary pump that is controllable in a synchronous copulsating or counterpulsating fashion, or in some out-of-phase intermediate thereof. In one application, it is contemplated that the present invention be applied such that the heart experiences a reduced pressure at the aortic root during systole (afterload) and/or a reduced left ventricular end diastolic pressure (pre-load), thus reducing the hemodynamic burden or workload on the heart and, thus, permitting the heart to recover.

It is contemplated that, where the entire system of the present invention is implanted, that it be implanted subcutaneously without the need for major invasive surgery and, preferably, extrathoracically. For example, the pump may be implanted in the groin area, with the inflow conduit attached to the femoral or iliac artery proximate thereto and the outflow conduit attached to the axillary artery proximate the shoulder. It is contemplated that the outflow conduit be applied by tunneling it under the skin from the pump to the axillary artery. Where implanted, the pump is preferably powered by an implantable power source, such as for example a battery, that may be regenerated externally by an RF induction system or be replaced periodically, and/or a self-generating power source that, for example, draws energy from the human body (e.g., muscles, chemicals, heat).

The present invention also comprises a method for supplementing the circulation of blood in the patient and potentially reducing the workload on the heart of a patient without connecting any component to the patient's heart. The inventive method comprises the steps of implanting a pump configured to generate blood flow at volumetric rates that are on average subcardiac, wherein the pump has an inflow and outflow conduit attached thereto; connecting a distal end of the inflow conduit to a first peripheral blood vessel with a minimally-invasive surgical procedure to permit the flow of blood to the pump from the first peripheral blood vessel of the patient; implanting the inflow conduit subcutaneously; connecting a distal end of the outflow conduit to a second peripheral blood vessel with a minimally-invasive surgical procedure to permit the flow of blood away from the pump to the second peripheral blood vessel of the patient; and operating said pump to perfuse blood through the patient's circulatory system. Where the second peripheral blood vessel is the axillary artery, the step of connecting the distal end of the outflow conduit is performed in such a manner that a sufficient flow of blood is directed toward the hand to avoid limb ischemia while ensuring that sufficient flow is directed toward the aorta without damaging the endothelial lining of the second peripheral blood vessel. The same concerns for avoiding limb ischemia and damage to the endothelial lining would apply, however, regardless of the selection of second peripheral blood vessel.

In one specific application, the pump is capable of synchronous control wherein the step of operating the pump includes the steps of beginning discharge of blood out of the pump during isovolumic contraction and discontinuing discharge of blood when the aortic valve closes following systole. Depending upon the patient and the specific arrangement of the present system, this specific method results in reduced afterload and/or preload on the heart while also supplementing circulation. For example, in one embodiment, the first and second blood vessels are the femoral and axillary arteries, respectively.

In an alternative method of applying the present invention, the pump is not implanted and the inflow and outflow conduits are connected to the first and second blood vessels percutaneously, using a readily-removable connector, such as a cannula, to connect the distal ends of each conduit to the blood vessels.

An important advantage of the present invention is that it utilizes the benefits of an IABP, without the requirement of extracorporeal equipment or the need to have a balloon or similar implement partially obstructing a blood vessel. In addition to the benefits of an IABP, it also offers the benefit of reducing the preload on the heart. The present invention thus offers simplicity and long-term use.

Another important advantage of the present invention is its potential to enhance mixing of systemic arterial blood, particularly in the aorta, and thereby deliver blood with a higher oxygen-carrying capacity to organs supplied by arterial side branches off of the aorta. This overcomes the problem of blood streaming in the descending aorta that may sometimes occur in patients suffering from low cardiac output or other ailments resulting in low blood flow. The lack of mixing of the blood within the descending aorta that may result from blood streaming could lead to a higher concentration of red blood cells and nutrients in the central region of the aorta and a decreasing concentration of red blood cells closer to the aortic wall. This could result in lower hematocrit blood flowing into branch arteries from the aorta. Where it is desired to address the potential problem of blood streaming, a method of utilizing the present invention may include taking steps to assess certain parameters of the patient and then to determine the minimum output of the pump that ensures turbulent flow in the aorta, thereby enhancing blood mixing. One embodiment of that method includes the step of determining the Reynolds number and the average Womersley number for the flow through the descending aorta before and/or after applying the present inventive system to the patient and adjusting the pump accordingly.

BRIEF DESCRIPTION OF THE DRAWINGS

These and other features and advantages of the invention will now be described with reference to the drawings, which are intended to illustrate and not to limit the invention.

DETAILED DESCRIPTION OF THE PREFERRED EMBODIMENT

Turning now to the drawings provided herein, a more detailed description of the embodiments of the present invention is provided below. It should be noted, however, that while some embodiments have all of the advantages identified herein, other embodiments may only realize some but not all of the advantages.

The present invention provides a heart assist system that is extracardiac in nature. In other words, the present invention supplements blood perfusion, without the need to interface directly with the heart and aorta. Thus, no major invasive surgery is necessary to use the present invention. The present invention also lessens the hemodynamic burden or workload on the heart by reducing the pressure at the aortic root during systole (afterload) and/or reducing left ventricular end diastolic pressure and volume (preload).

Figure 1:
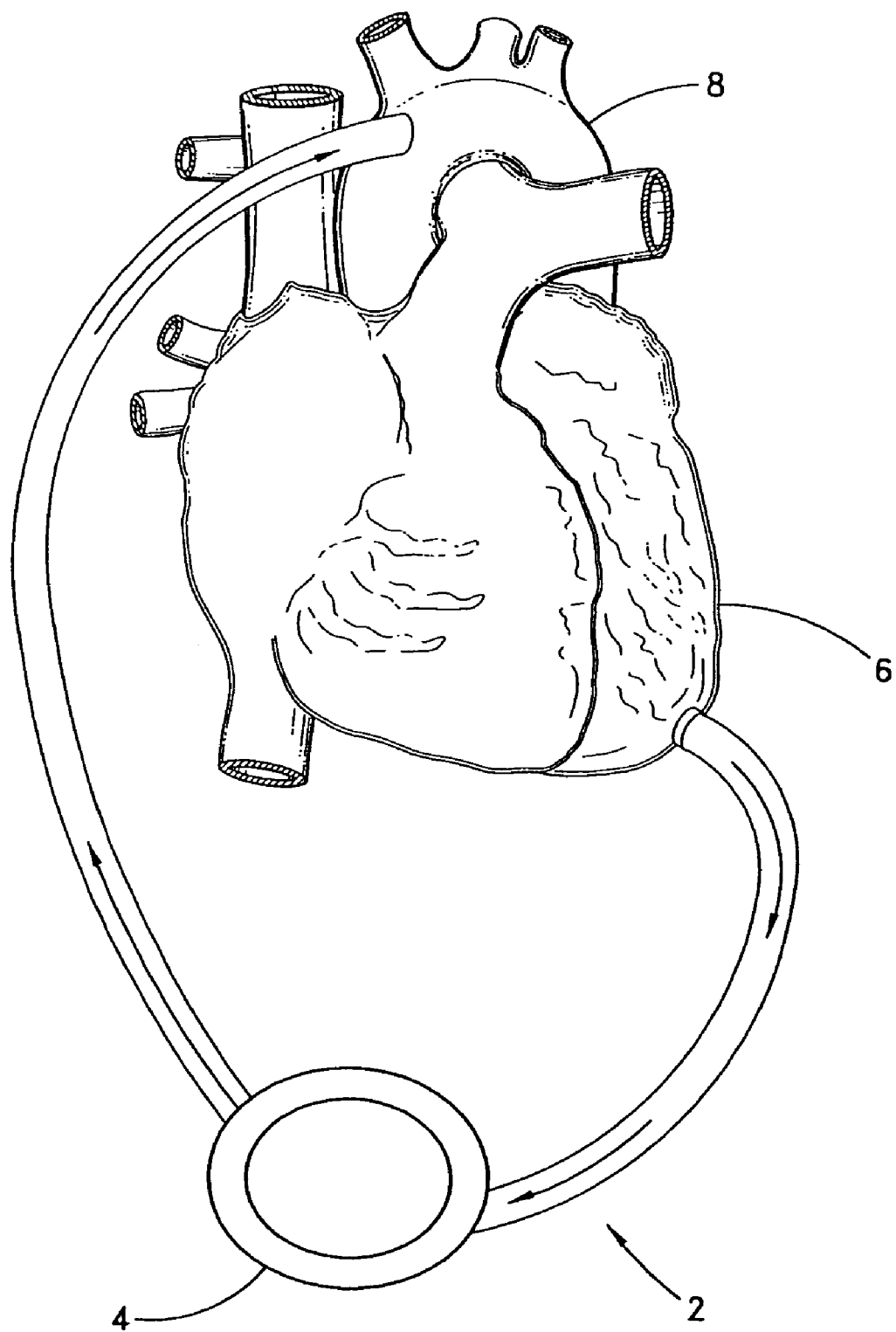
FIG. 1 is a schematic view of a cardiac assist device, known as a left ventricular assist device, showing a bypass from the apex of the left ventricle to the aortic arch.
Figure 2:
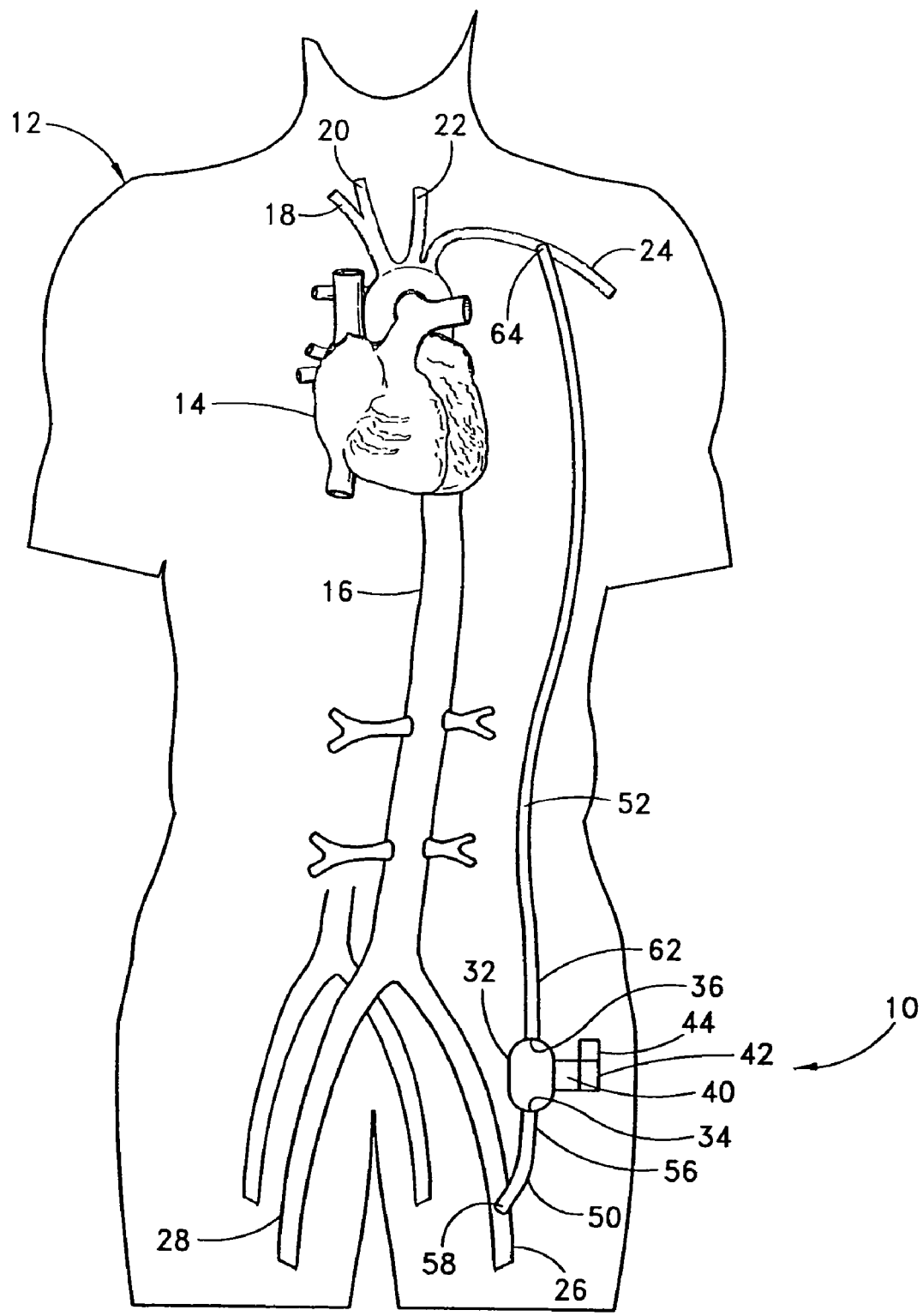
FIG. 2 is a schematic view of a first embodiment of the present invention, shown applied to a patient's circulatory system.

With reference to FIG. 2, a first embodiment of the present invention 10 is shown applied to a patient 12 having an ailing heart 14 and an aorta 16, from which peripheral brachiocephalic blood vessels extend, including the right subclavian 18, the right carotid 20, the left carotid 22, and the left axillary 24. Extending from the descending aorta is another set of peripheral blood vessels, the left and right femoral arteries 26, 28.

The first embodiment 10 comprises a pump 32, having an inlet 34 and an outlet 36 for connection of flexible conduits thereto. The pump 32 is preferably a rotary pump, either an axial type or a centrifugal type, although other types of pumps may be used, whether commercially-available or customized. In either case, the pump should be sufficiently small to be implanted subcutaneously and preferably extrathoracically, for example in the groin area of the patient, without the need for major invasive surgery. Because the present invention is an extracardiac system, no valves are necessary. Any inadvertent backflow through the pump and/or through the inflow conduit would not harm the patient.

Regardless of the style or nature chosen, the pump 32 of the present invention is sized to generate blood flow at subcardiac volumetric rates, less than about 50% of the flow rate of an average healthy heart, although flow rates above that may be effective. Thus, the pump 32 of the present invention is sized and configured to discharge blood at volumetric flow rates anywhere in the range of 0.1 to 3 liters per minute, depending upon the application desired and/or the degree of need for heart assist. For example, for a patient experiencing advanced congestive heart failure, it may be preferable to employ a pump that has an average subcardiac rate of 2.5 to 3 liters per minute. In other patients, particularly those with minimal levels of heart failure, it may be preferable to employ a pump that has an average subcardiac rate of 0.5 liters per minute or less. In yet other patients it may be preferable to employ a pump that is a pressure wave generator that uses pressure to augment the flow of blood generated by the heart.

In one embodiment, the pump selected is a continuous flow pump so that blood perfusion through the circulation system is continuous. In an alternative embodiment, the pump selected has the capability of synchronous actuation; i. e., it may be actuated in a pulsatile mode, either in copulsating or counterpulsating fashion.

For copulsating action, it is contemplated that the pump 32 would be actuated to discharge blood generally during systole, beginning actuation, for example, during isovolumic contraction before the aortic valve opens or as the aortic valve opens. The pump would be static while the aortic valve is closed following systole, ceasing actuation, for example, when the aortic valve closes.

For counterpulsating actuation, it is contemplated that the pump 32 would be actuated generally during diastole, ceasing actuation, for example, before or during isovolumic contraction. Such an application would permit and/or enhance coronary blood perfusion. In this application, it is contemplated that the pump would be static during the balance of systole after the aortic valve is opened, to lessen the burden against which the heart must pump. The aortic valve being open encompasses the periods of opening and closing, wherein blood is flowing therethrough.

It should be recognized that the designations copulsating and counterpulsating are general identifiers and are not limited to specific points in the patient's heart cycle when the pump begins and discontinues actuation. Rather, they are intended to generally refer to pump actuation in which the pump is actuating, at least in part, during systole and diastole, respectively. For example, it is contemplated that the pump might be activated to be out of phase from true copulsating or counterpulsating actuation described herein, and still be synchronous, depending upon the specific needs of the patient or the desired outcome. One might shift actuation of the pump to begin prior to or after isovolumic contraction or to begin before or after isovolumic expansion.

Furthermore, the pulsatile pump may be actuated to pulsate asynchronously with the patient's heart. Typically, where the patient's heart is beating irregularly, there may be a desire to pulsate the pump asynchronously so that the perfusion of blood by the extracardiac pumping system is more regular and, thus, more effective at oxygenating the organs. Where the patient's heart beats regularly, but weakly, synchronous pulsation of the extracardiac pump may be preferred.

The pump 32 is driven by a motor 40 and/or other type of drive means and is controlled preferably by a programmable controller 42 that is capable of actuating the pump in pulsatile fashion, where desired, and also of controlling the speed or output of the pump. For synchronous control, the patient's heart would preferably be monitored with an EKG in which feedback would be provided the controller 42. The controller 42 is preferably programmed by the use of external means. This may be accomplished, for example, using RF telemetry circuits of the type commonly used within implantable pacemakers and defibrillators. The controller may also be auto-regulating to permit automatic regulation of the speed, and/or regulation of the synchronous or asynchronous pulsation of the pump, based upon feedback from ambient sensors monitoring parameters, such as pressure or the patient's EKG. It is also contemplated that a reverse-direction pump be utilized, if desired, in which the controller is capable of reversing the direction of either the drive means or the impellers of the pump. Such a pump might be used where it is desirable to have the option of reversing the direction of circulation between two peripheral blood vessels.

Power to the motor 40 and controller 42 may be provided by a power source 44, such as a battery, that is preferably rechargeable by an external induction source (not shown), such as an RF induction coil that may be electromagnetically coupled to the battery to induce a charge therein. Alternative power sources are also possible, including a device that draws energy directly from the patient's body; e. g., the patient's muscles, chemicals or heat. The pump can be temporarily stopped during recharging with no appreciable life threatening effect, because the system only supplements the heart, rather than substituting for the heart.

While the controller 42 and power source 44 are preferably pre-assembled to the pump 32 and implanted therewith, it is also contemplated that the pump 32 and motor 40 be implanted at one location and the controller 42 and power source 44 be implanted in a separate location. In one alternative arrangement, the pump 32 may be driven externally through a percutaneous drive line. In another alternative, the pump, motor and controller may be implanted and powered by an extracorporeal power source. In the latter case, the power source could be attached to the side of the patient to permit fully ambulatory movement.

The inlet 34 of the pump 32 is preferably connected to a flexible inflow conduit 50 and a flexible outflow conduit 52 to direct blood flow from one peripheral blood vessel to another. The inflow and outflow conduits 50, 52 may, for example, be formed from Dacron, Hemashield or Gortex materials, although other synthetic materials may be suitable. The inflow and outflow conduits 50, 52 may also comprise biologic materials or pseudobiological (hybrid) materials (e. g., biologic tissue supported on a synthetic scaffold). The inflow and outflow conduits are preferably configured to minimize kinks so blood flow is not meaningfully interrupted by normal movements of the patient or compressed easily from external forces. In some cases, the inflow and/or outflow conduits may come commercially already attached to the pump. Where it is desired to implant the pump 32 and the conduits 50, 52, it is preferable that the inner diameter of the conduits be less than 25 mm, although diameters slightly larger may be effective.

In one preferred application of the present invention, the first embodiment is applied in an arterial-arterial fashion; for example, as a femoral-axillary connection, as is shown in FIG. 2. It should be appreciated by one of ordinary skill in the art that an axillary-femoral connection would also be effective using the embodiments described herein. Indeed, it should be recognized by one of ordinary skill in the art that the present invention might be applied to any of the peripheral blood vessels in the patient.

The inflow conduit 50 has a first proximal end 56 that connects with the inlet 34 of the pump 32 and a second distal end 58 that connects with a first peripheral blood vessel, which is preferably the left femoral artery 26 of the patient 12, although the right femoral artery or any other peripheral artery may be acceptable. In one application, the connection between the inflow conduit 50 and the first blood vessel is via an end-to-side anastomosis, although a side-to-side anastomosis connection might be used mid-stream of the conduit where the inflow conduit were connected at its second end to an additional blood vessel or at another location on the same blood vessel (neither shown).

Similarly, the outflow conduit 52 has a first proximal end 62 that connects to the outlet 36 of the pump 32 and a second distal end 64 that connects with a second peripheral blood vessel, preferably the left axillary artery 24 of the patient 12, although the right axillary artery, or any other peripheral artery, would be acceptable. In one application, the connection between the outflow conduit 52 and the second blood vessel is via an end-to-side anastomosis, although a side-to-side anastomosis connection might be used mid-stream of the conduit where the outflow conduit were connected at its second end to yet another blood vessel (not shown) or at another location on the same blood vessel. Preferably, the outflow conduit is attached to the second blood vessel at an angle that results in the predominant flow of blood out of the pump proximally toward the aorta and heart, such as is shown in FIG. 2, while still maintaining sufficient flow distally toward the hand to prevent limb ischemia.

It is preferred that application of the present invention to the peripheral blood vessels be accomplished subcutaneously; i. e., at a shallow depth just below the skin or first muscle layer so as to avoid major invasive surgery. It is also preferred that the present invention be applied extrathoracically to avoid the need to invade the patient's chest cavity. Where desired, the entire extracardiac system of the present invention 10 may be implanted within the patient 12. In that case, the pump 32 may be implanted, for example, into the groin area, with the inflow conduit 50 connected subcutaneously to, for example, the femoral artery 26 proximate the pump 32. The outflow conduit would be tunneled subcutaneously through to, for example, the left axillary artery 24. In an alternative arrangement, the pump 32 and associated drive and controller could be temporarily fastened to the exterior skin of the patient, with the inflow and outflow conduits 50, 52 connected percutaneously. In either case, the patient may be ambulatory without restriction of tethered lines.

Figure 3:
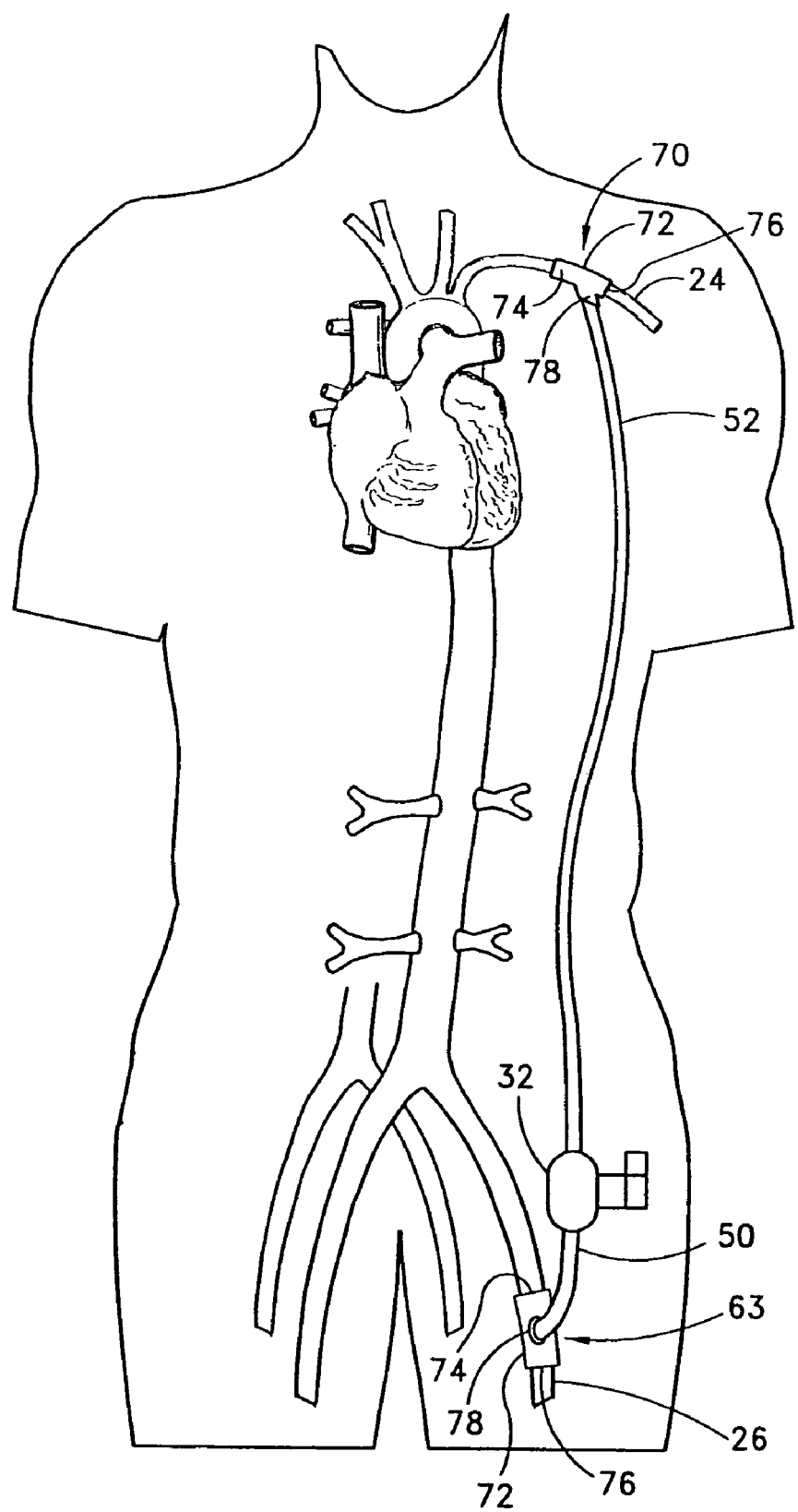
FIG. 3 is a schematic view of a second embodiment of the present invention, shown applied to a patient's circulatory system.

It is contemplated that, where an anastomosis connection is not desired, a special connector may be used to connect the conduits 50, 52 to the peripheral blood vessels. With reference to FIG. 3, a second embodiment of the present invention is shown, wherein the inflow conduit 50 and outflow conduit 52 are connected to the peripheral blood vessels via first and second connectors 68, 70 each comprising three-opening fittings. In the preferred embodiment, the connectors 68, 70 comprise an intra-vascular, generally-tee-shaped fitting 72 having a proximal end 74, a distal end 76, and an angled divergence 78 permitting connection to the inflow and outflow conduits 50, 52 and the blood vessels. The proximal and distal ends 74, 76 of the fittings 72 permit connection to the blood vessel into which the fitting is positioned. The angle of divergence 78 of the fittings 72 may be 90 degrees or less in either direction from the axis of flow through the blood vessel, as optimally selected to generate the needed flow distally toward the hand to prevent limb ischemia, and to insure sufficient flow and pressure toward the aorta to provide the circulatory assistance and workload reduction needed while minimizing or avoiding endothelial damage to the vessel. In another embodiment, the connectors 68, 70 are sleeves (not shown) that surround and attach to the outside of the peripheral blood vessel where, within the interior of the sleeve, a port to the blood vessel is provided to permit blood flow from the conduits 50, 52 when they are connected to the connectors 68, 70, respectively.

Figure 7:
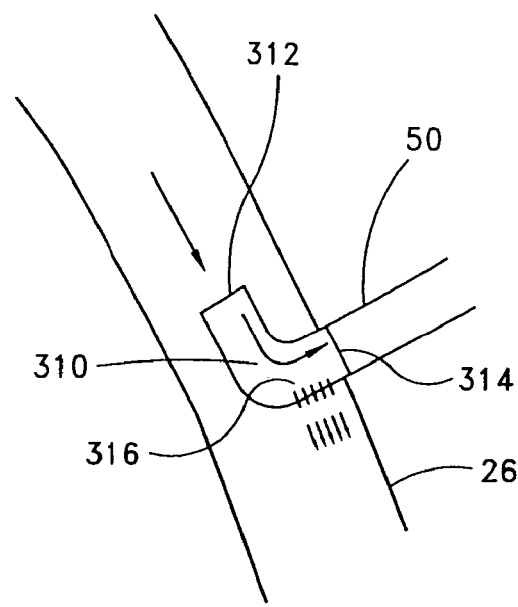
FIG. 7 is a schematic view of an inflow L-shaped connector, shown inserted within a blood vessel.

Other types of connectors having other configurations are contemplated that may avoid the need for an anastomosis connection or that permit connection of the conduits to the blood vessels. For example, it is contemplated that an L-shaped connector be used if it is desired to withdraw blood more predominantly from one direction of a peripheral vessel or to direct blood more predominantly into a peripheral vessel. Referring to FIG. 7, an inflow conduit 50 is fluidly connected to a peripheral vessel, for example, the left femoral artery 26, using an L-shaped connector 310. The connector 310 has an inlet port 312 at a proximal end and an outlet port 314 through which blood flows into the inflow conduit 50. The connector 310 also has an arrangement of holes 316 within a wall positioned at a distal end opposite the inlet port 312 so that some of the flow drawn into the connector 310 is diverted through the holes 312, particularly downstream of the connector, as in this application. A single hole in the wall could also be effective, depending upon size and placement. The connector may be a deformable L-shaped catheter percutaneously applied to the blood vessel or, in an alternative embodiment, be connected directly to the walls of the blood vessel for more long term application. By directing some blood flow downstream of the connector during withdrawal of blood from the vessel, ischemic damage downstream from the connector may be avoided. Such ischemic damage might otherwise occur if the majority of the blood flowing into the inflow connector were diverted from the blood vessel into the inflow conduit. It is also contemplated that a connection to the blood vessels might be made via a cannula, wherein the cannula is implanted, along with the inflow and outflow conduits.

The advantage of discrete connectors is their potential application to patients with chronic CHF. A connector eliminates a need for an anastomosis connection between the conduits of the present invention system and the peripheral blood vessels where it is desired to remove and/or replace the system more than one time. The connectors could be applied to the first and second blood vessels semi-permanently, with an end cap applied to the divergence for later quick-connection of the present invention system to the patient. In this regard, a patient might experience the benefit of the present invention periodically, without having to reconnect and rediscannect the conduits from the blood vessels via an anastomosis procedure each time. Each time it is desired to implement the present invention, the end caps would be removed and the conduit attached to the connectors quickly.

In the preferred embodiment of the connector 70, the divergence 78 is oriented at an acute angle significantly less than 90 degree from the axis of the fitting 72, as shown in FIG. 3, so that a majority of the blood flowing through the outflow conduit 52 into the blood vessel (e. g., left axillary 24) flows in a direction proximally toward the heart 14, rather than in the distal direction. In an alternative embodiment, the proximal end 74 of the fitting 72 may have a diameter larger than the diameter of the distal end 76, without need of having an angled divergence, to achieve the same result.

With or without a connector, with blood flow directed proximally toward the aorta, the result may be concurrent flow down the descending aorta, which will result in the reduction of pressure at the aortic root. Thus, the present invention may be applied so to reduce the afterload on the patient's heart, permitting at least partial if not complete CHF recovery, while supplementing blood circulation. Concurrent flow depends upon the phase of operation of the pulsatile pump and the choice of second blood vessel to which the outflow conduit is connected.

Figure 4:
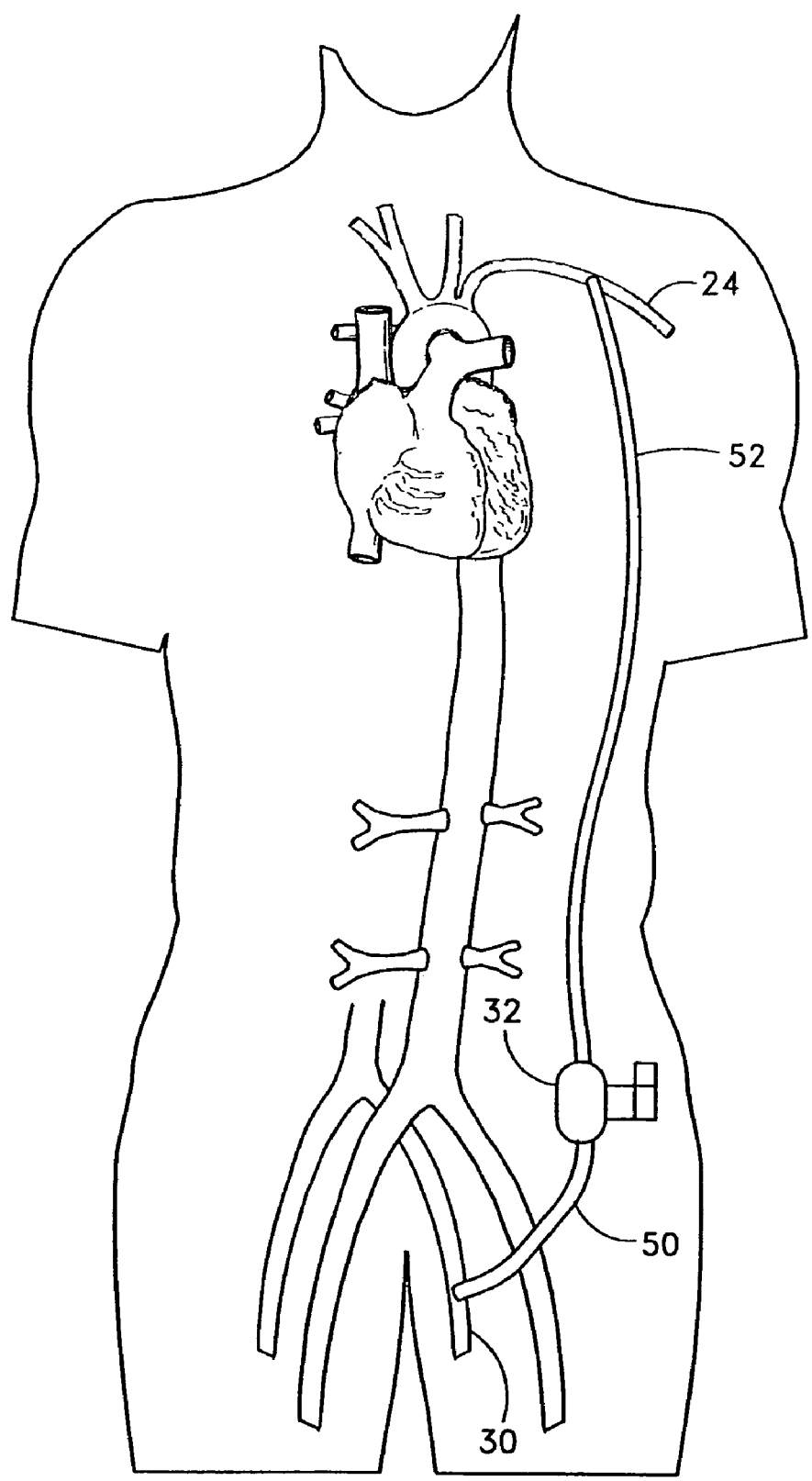
FIG. 4 is a schematic view of a variation of the first embodiment of FIG. 2 shown implanted into a patient.

While the present invention may be applied to create an arterial-arterial flow path, given the nature of the present invention, i. e., supplementation of circulation to meet organ demand, a venous-arterial flow path may also be used. For example, with reference to FIG. 4, one embodiment of the present invention 10 may be applied to the patient 12 such that the inflow conduit 50 is connected to a peripheral vein, such as the left femoral vein 80. In this arrangement, the outflow conduit 50 may be connected to one of the peripheral arteries, such as the left axillary 24. Arterial-venous arrangements are contemplated as well. In those venous-arterial cases where the inflow is connected to a vein and the outflow is connected to an artery, the pump 32 should be sized to permit flow sufficiently small so that oxygen-deficient blood does not rise to unacceptable levels in the arteries. It should be appreciated that the connections to the peripheral veins could be by one or more methods described above for connecting to a peripheral artery. It should also be appreciated that the present invention could be applied as a venous-venous flow path, wherein the inflow and outflow are connected to separate peripheral veins. In addition, an alternative embodiment comprises two discrete pumps and conduit arrangements, one being applied as a venous-venous flow path, and the other as an arterial-arterial flow path. When venous blood is mixed with arterial blood either at the inlet of the pump or the outlet of the pump the ratio of venous blood to arterial blood should be controlled to maintain an arterial saturation of a minimum of 80% at the pump inlet or outlet. Arterial saturation can be measured and/or monitored by pulse oximetry, laser doppler, colorimetry or other methods used to monitor blood oxygen saturation. The venous blood flow into the system can then be controlled by regulating the amount of blood allowed to pass through the conduit from the venous-side connection.

Figure 5:
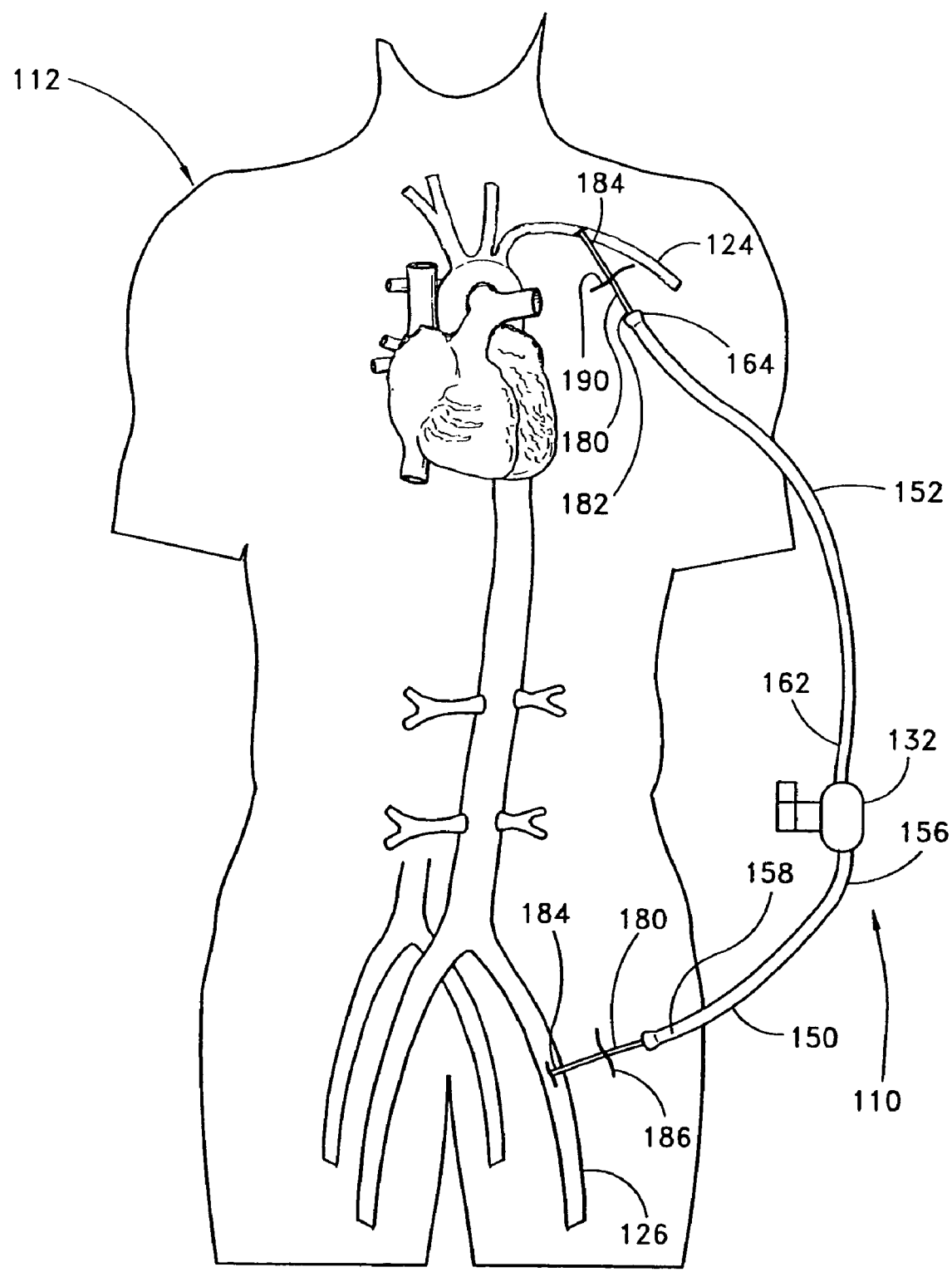
FIG. 5 is a schematic view of a third embodiment of the present invention, shown applied to a patient's circulatory system.

A partial external application of the present invention is contemplated where a patient's heart failure is acute; i. e., is not expected to last long, or in the earlier stages of heart failure (where the patient is in New York Heart Association Classification (NYHAC) functional classes II or III). With reference to FIG. 5, a third embodiment of the present invention 110 is applied percutaneously to a patient 112 to connect two peripheral blood vessels wherein a pump 132 and its associated driving means and controls are employed extracorporeally. The pump 132 has an inflow conduit 150 and an outflow conduit 152 associated therewith for connection to two peripheral blood vessels. The inflow conduit 150 has a first end 156 and second end 158 wherein the second end is connected to a first peripheral blood vessel (e. g., femoral artery 126) by way of a cannula 180. The cannula 180 has a first end 182 sealably connected to the second end 158 of the inflow conduit 150. The cannula 180 also has a second end 184 that is inserted through a surgical opening 186 or an introducer sheath (not shown) and into the blood vessel source (e. g., femoral artery 126).

Similarly, the outflow conduit 152 has a first end 162 and second end 164 wherein the second end is connected to a second peripheral blood vessel (e. g., left axillary artery 124) by way of a cannula 180. Like the inflow cannula, the outflow cannula 180 has a first end 182 sealably connected to the second end 164 of the outflow conduit 152. The outflow cannula 180 also has a second end 184 that is inserted through surgical opening 190 or an introducer sheath (not shown) and into the second blood vessel (e. g., left axillary artery 124). By use of a percutaneous application, the present invention may be applied temporarily without the need to implant any aspect thereof or to make anastomosis connections to the blood vessels.

Figure 9:
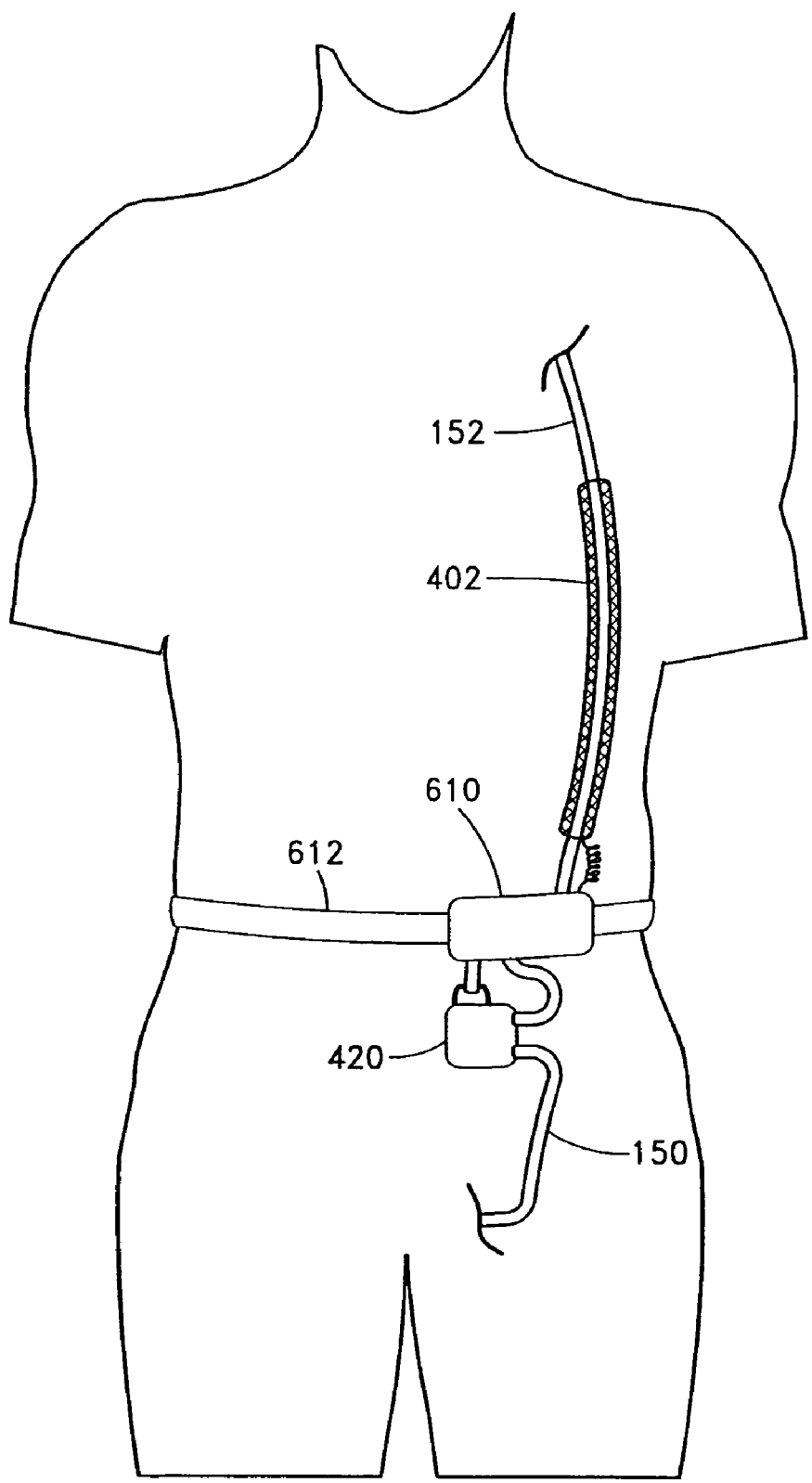
FIG. 9 is a schematic view of a sixth embodiment of the present invention showing a reservoir and a portable housing for carrying a portion of the invention directly on the patient.

It is contemplated that a means for minimizing the loss of thermal energy in the patient's blood be provided where the present inventive system is applied extracorporeally. Such means for minimizing the loss of thermal energy may comprise, for example, a heated bath through which the inflow and outflow conduits pass or, alternatively, thermal elements secured to the exterior of the inflow and outflow conduits. Referring to FIG. 9, one embodiment comprises an insulating wrap 402 surrounding the outflow conduit 152 having one or more thermal elements passing therethrough. The elements may be powered, for example, by a battery (not shown). One advantage of thermal elements is that the patient may be ambulatory, if desired. Other means that are known by persons of ordinary skill in the art for ensuring that the temperature of the patient's blood remains at acceptable levels while travelling extracorporeally are also contemplated.

An alternative variation of the third embodiment may be used where it is desired to treat a patient periodically, but for short periods of time each occasion and without the use of special connectors. With this variation, it is contemplated that the second ends of the inflow and outflow conduits be more permanently connected to the associated blood vessels via, for example, an anastomosis connection, wherein a portion of each conduit proximate to the blood vessel connection is implanted percutaneously with a removable cap enclosing the eternally-exposed first end (or an intervening end thereof) of the conduit external to the patient. When it is desired to provide a circulatory flow path to supplement blood flow, the removable cap on each exposed percutaneously-positioned conduit could be removed and the pump (or the pump with a length of inflow and/or outflow conduit attached thereto) inserted between the exposed percutaneous conduits. In this regard, a patient may experience the benefit of the present invention periodically, without having to reconnect and redisconnect the conduits from the blood vessels each time.

Figure 6:
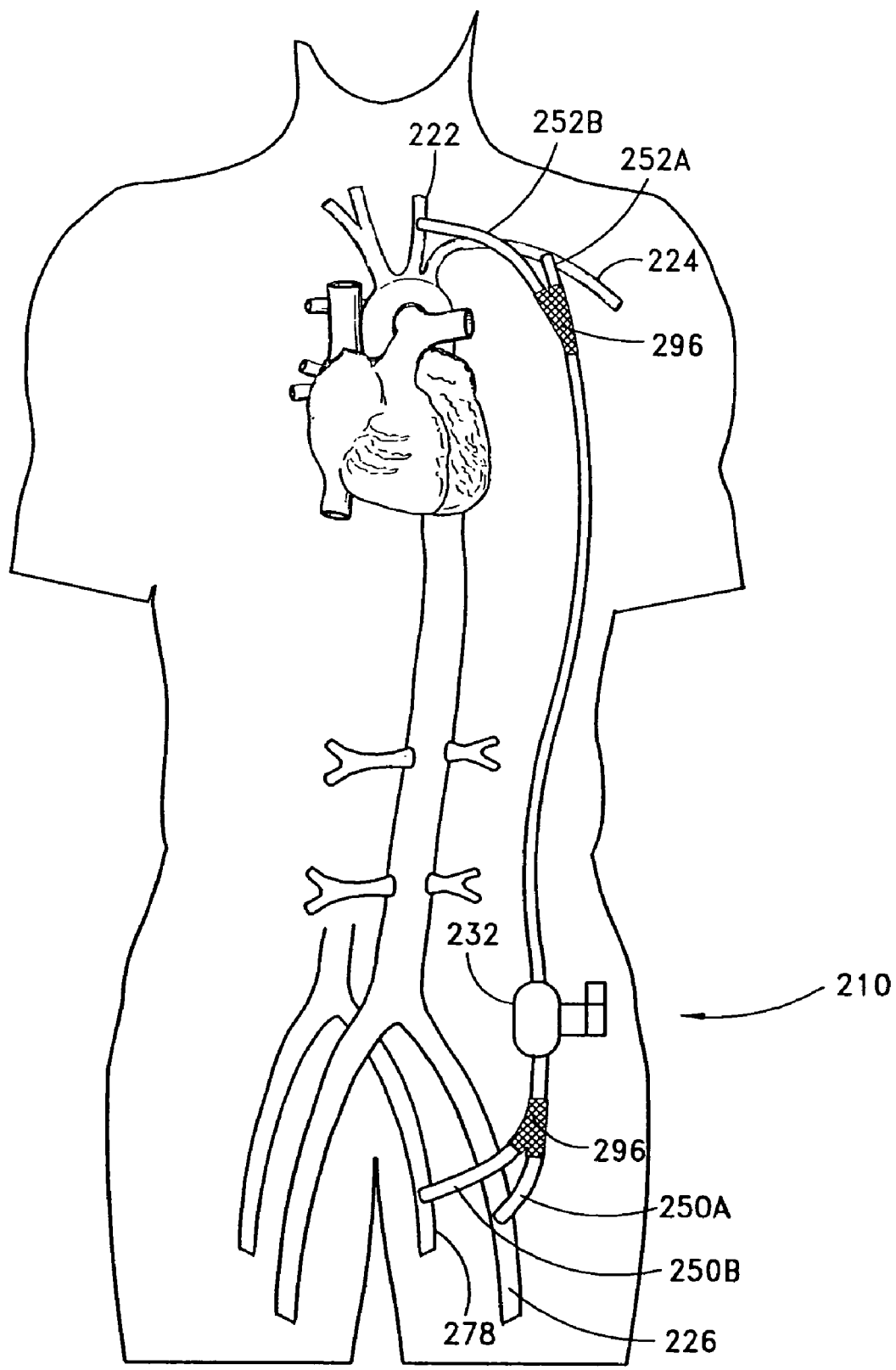
FIG. 6 is a schematic view of a fourth embodiment of the present invention, shown applied to a patient's circulatory system.

Another embodiment of the present invention includes a plurality of inflow and/or outflow conduits. For example, with reference to FIG. 6, a fourth embodiment of the present invention 210 includes a pump 232 in fluid communication with a plurality of inflow conduits 250A, 250B and a plurality of outflow conduits 252A, 252B. Each pair of conduits converges at a generally Y-shaped convergence 296 that converges the flow at the inflow end and diverges the flow at the outflow end. Each conduit may be connected to a separate peripheral blood vessel, although it is possible to have two connections to the same blood vessel at remote locations. In one arrangement, all four conduits are connected to peripheral arteries. Alternatively, one or more of the conduits could be connected to veins. In the application shown in FIG. 6, inflow conduit 250A is connected to left femoral artery 226 while inflow conduit 250B is connected to left femoral vein 278. Outflow conduit 252A is connected to left axillary artery 224 while outflow conduit 252B is connected to left carotid artery 222.

It should be noted that the connections of any or all of the conduits to the blood vessels may be via an anastomosis connection or via a special connector, as described above. In addition, the embodiment of FIG. 6 may be applied to any combination of peripheral blood vessels that would best suit the patient's condition. For example, it may be desired to have one inflow conduit and two outflow conduits or vice versa. It should be noted that more than two conduits may be used on the inflow or outflow side, where the number of inflow conduits is not necessarily equal to the number of outflow conduits.

If desired, the present inventive system may further comprise a reservoir that is either contained within or in fluid communication with the inflow conduit. This reservoir is preferably made of materials that are nonthrombogenic. Referring to FIG. 9, a reservoir 420 is positioned fluidly in line with the inflow conduit 150. The reservoir 420 serves to sustain adequate blood in the system when the pump demand exceeds momentarily the volume of blood available in the peripheral blood vessel in which the inflow conduit resides until the pump output can be adjusted. The reservoir reduces the risk of excessive drainage of blood from the peripheral blood vessel, which may occur when cardiac output falls farther than the already diminished baseline level of cardiac output, or when there is systemic vasodilation, as can occur, for example, with septic shock. It is contemplated that the reservoir would be primed with an acceptable solution, such as saline, when the present system is first applied to the patient.

Figure 8:
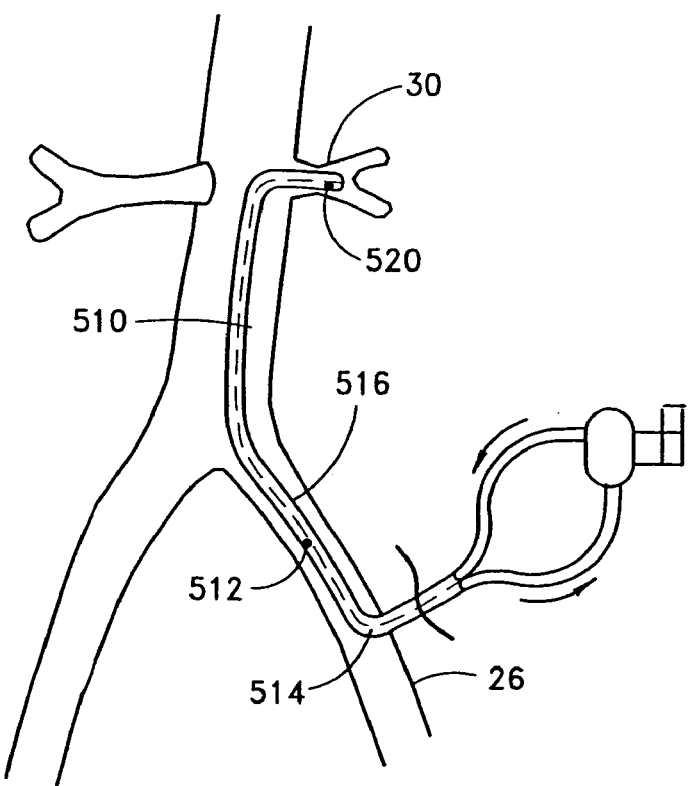
FIG. 8 is a schematic view of a fifth embodiment of the present invention employing a multi-lumen catheter for single site application to a patient.

In an alternative embodiment, the present system comprises a multi-lumen catheter whereby the system may be applied by insertion at a single cannulated site while the inflow and outflow conduits still fluidly communicate with peripheral vessels. Referring to FIG. 8, a multi-lumen catheter 510 could be inserted, for example, into the left femoral artery 26 and guided superiorly through the descending aorta to one of numerous locations. The blood could discharge, for example, directly into the descending aorta proximate an arterial branch, such as the left subclavian artery or, as shown in FIG. 2 by way of example, directly into the peripheral mesenteric artery 30. Preferably, the multi-lumen catheter 510 has an inflow port 512 that may be positioned within the left femoral artery 26 when the catheter 510 is fully inserted so that blood drawn from the left femoral artery is directed through the inflow port 512 into a first lumen 514 in the catheter. This blood is then pumped through a second lumen 516 in the catheter and out through an outflow port 520 at the distal end of the catheter 510. The outflow port 520 may be situated within, for example, the mesenteric artery 30 such that blood flow results from the left femoral artery 26 to the mesenteric artery 30. Preferably, where there is a desire for the patient to be ambulatory, the multi-lumen catheter 510 should preferably be made of material sufficiently flexible and resilient to permit the patient to be comfortably move about while the catheter is indwelling in the patient's blood vessels without causing any vascular trauma.

As explained above for several embodiments, one of the advantages of the present heart assist system is that it permits the patient to be ambulatory. If desired, the system may be designed portably so that it may be carried directly on the patient. Referring to FIG. 9, this may be accomplished through the use of a portable case 610 with a belt strap 612 to house the pump, power supply and/or the controller, along with certain portions of the inflow and/or outflow conduits, if necessary. It may also be accomplished with a shoulder strap or other techniques, such as a backpack or a fanny pack, that permit effective portability. As shown in FIG. 9, blood is drawn through the inflow conduit 150 into a pump contained within the portable case 610, where it is discharged into the outflow conduit 152 back into the patient.

An important advantage of the present invention is its potential to enhance mixing of systemic arterial blood, particularly in the aorta. Such enhanced mixing ensures the delivery of blood with higher oxygen-carrying capacity to organs supplied by arterial side branches off of the aorta. A method of enhancing mixing utilizing the present invention preferably includes taking steps to assess certain parameters of the patient and then to determine the minimum output of the pump that, when combined with the heart output, ensures turbulent flow in the aorta, thereby enhancing blood mixing.

Blood flow in the aortic arch during normal cardiac output may be characterized as turbulent in the end systolic phase. It is known that turbulence in a flow of fluid through pipes and vessels enhances the uniform distribution of particles within the fluid. It is believed that turbulence in the descending aorta enhances the homogeneity of blood cell distribution in the aorta. It is also known that laminar flow of viscous fluids leads to a higher concentration of particulates in the central portion of pipes and vessels through which the fluid flows. It is believed that, in low flow states such as that experienced during heart failure, there is reduced or inadequate mixing of blood cells leading to a lower concentration of nutrients at the branches of the aorta to peripheral organs and tissues. As a result, the blood flowing into branch arteries off of the aorta will likely have a lower hematocrit, especially that flowing into the renal arteries, the celiac trunk, the spinal arteries, and the superior and inferior mesenteric arteries. That is because these branches draw from the periphery of the aorta The net effect of this phenomenon is that the blood flowing into these branch arteries has a lower oxygen-carrying capacity, because oxygen-carrying capacity is directly proportional to both hematocrit and the fractional $O_2$ saturation of hemoglobin. Under those circumstances, it is very possible that these organs will experience ischemia-related pathology.

The phenomenon of blood streaming in the aorta, and the resultant inadequate mixing of blood resulting in central lumenal concentration of blood cells, is believed to occur when the Reynolds number ($N_R$) for the blood flow in the aorta is below 2300. To help ensure that adequate mixing of blood will occur in the aorta to prevent blood cells from concentrating in the center of the lumen, a method of applying the present invention to a patient may also include steps to adjust the output of the pump to attain turbulent flow within the descending aorta upstream of the organ branches; i.e., flow exhibiting a peak Reynolds number of at least 2300 within a complete cycle of systole and diastole. Because flow through a patient is pulsatile in nature, and not continuous, consideration must be given to how frequently the blood flow through the aorta has reached a certain desired velocity and, thus, a desired Reynolds number. The method contemplated herein, therefore, should also include the step of calculating the average Womersley number ($N_W$), which is a function of the frequency of the patient's heart beat. It is desired that a peak Reynolds number of at least 2300 is attained when the corresponding Womersley number for the same blood flow is approximately 6 or above.

More specifically, the method may comprise calculating the Reynolds number for the blood flow in the descending aorta by determining the blood vessel diameter and both the velocity and viscosity of the fluid flowing through the aorta. The Reynolds number may be calculated pursuant to the following equation:

$$N_R = \frac{V \cdot d}{\upsilon}$$

where: V=the velocity of the fluid; d=the diameter of the vessel; and $\upsilon$=the viscosity of the fluid. The velocity of the blood flowing through the aorta is a function of the cross-sectional area of the aorta and the volume of flow therethrough, the latter of which is contributed both by the patient's own cardiac output and by the output of the pump of the present invention. Velocity may be calculated by the following equation:

$$V = \frac{Q}{\pi r^2}$$

where Q=the volume of blood flowing through the blood vessel per unit time, e. g., the aorta, and r=radius of the aorta. If the relationship between the pump output and the velocity is already known or independently determinable, the volume of blood flow Q may consist only of the patient's cardiac output, with the knowledge that that output will be supplemented by the subcardiac pump that is part of the present invention. If desired, however, the present system can be implemented and applied to the patient first, before calculating Q, which would consist of the combination of cardiac output and the pump output.

The Womersley number may be calculated as follows:

$$N_W = r\sqrt{2\pi\omega/\upsilon}$$

where r is the radius of the vessel being assessed, $\omega$ is the frequency of the patient's heartbeat, and $\upsilon$=the viscosity of the fluid. For a peak Reynolds number of at least 2300, a Womersley number of at least 6 is preferred, although a value as low as 5 would be acceptable.

By determining (i) the viscosity of the patient's blood, which is normally about 3.0 $mm^2$/sec (kinematic viscosity), (ii) the cardiac output of the patient, which of course varies depending upon the level of CHF, and (iii) the diameter of the patient's descending aorta, which varies from patient to patient but is about 21 mm for an average adult, one can determine the flow rate Q that would result in a velocity through the aorta necessary to attain a Reynolds number of at least 2300 at its peak during the patient's heart cycle. Based upon that determination of Q, one may adjust the output of the pump of the present invention to attain the desired turbulent flow characteristic through the aorta, enhancing mixing of the blood therethrough.

One may use ultrasound (e. g., echocardiography or abdominal ultrasound) to measure the diameter of the aorta, which is relatively uniform in diameter from its root to the abdominal portion of the descending aorta. Furthermore, one may measure cardiac output using a thermodilution catheter or other techniques known to those of skill in the art. Finally, one may measure viscosity of the patient's blood by using known methods; for example, using a capillary viscosimeter. It is expected that in many cases, the application of this embodiment of the present method will provide a basis to more finely tune the system to more optimally operate the system to the patient's benefit. Other methods contemplated by the present invention may include steps to assess other patient parameters that enable a person of ordinary skill in the art to optimize the present system to ensure adequate mixing within the vascular system of the patient.

While the above description has explained the inventive features of the invention as applied to various embodiments, it will be understood that the variations in the form and details of the apparatus or method may be made by those of ordinary skill in the art without departing from the spirit of the invention. The scope of the invention is indicated by the appended claims herein, however, not by the foregoing description.

What is claimed is:

1. A method for increasing perfusion in a branch artery, the method comprising:
   providing fluid communication between a pump and an inflow conduit and between the pump and an outflow conduit;
   fluidly coupling said inflow conduit with a first location of the vasculature using a minimally invasive surgical procedure;
   advancing a distal end of the outflow conduit to a location proximate a branch artery; and
   operating said pump to direct blood from the first location to the branch artery at volumetric rates that are on average subcardiac to increase perfusion through the branch artery;
   wherein fluidly coupling the inflow conduit comprises fluidly coupling the inflow conduit to a first femoral artery.

2. A system for branch artery perfusion comprising:
   a pump configured to pump blood through a patient at subcardiac volumetric rates, said pump having an average flow rate that, during normal operation thereof, is substantially below that of the patient's heart when healthy;
   an inflow conduit comprising flexible tubing having an inner diameter that is less than 25 millimeters fluidly coupled to the pump to direct blood to the pump from a first non-primary blood vessel of the vasculature of the patient; and,
   an outflow conduit fluidly coupled to the pump and configured to direct blood directly into a branch artery to maintain or enhance blood flow to an organ or tissue supplied by the branch artery, wherein the outflow conduit is configured to be insertable into a renal artery;
   whereby connection of at least one of the inflow and outflow conduits to the vasculature may be made subcutaneously to permit application thereof in a minimally-invasive procedure.

3. The system of claim 2, wherein the inflow conduit defines a first lumen of a multilumen catheter and the outflow conduit defines a second lumen of the multilumen catheter.

4. The system of claim 2, wherein the outflow conduit is a cannula.

5. The system of claim 2, further comprising a cannula coupled with the outflow conduit.

6. The system of claim 2, wherein the inflow conduit is configured to couple with a femoral artery.

7. The system of claim 2, wherein the pump is configured to be implantable subcutaneously.

8. The system of claim 2, wherein the pump is capable of providing pulsatile flow.

9. The system of claim 2, wherein the pump has an average flow rate of between about 0.1 and about 3 liters per minute.

10. A system for branch artery perfusion comprising:
    a pump configured to pump blood through a patient at subcardiac volumetric rates, said pump having an average flow rate that, during normal operation thereof, is substantially below that of the patient's heart when healthy;
    an inflow conduit comprising flexible tubing having an inner diameter that is less than 25 millimeters fluidly coupled to the pump to direct blood to the pump from a first non-primary blood vessel of the vasculature of the patient; and,
    an outflow conduit fluidly coupled to the pump and configured to direct blood directly into a branch artery to maintain or enhance blood flow to an organ or tissue supplied by the branch artery wherein the outflow conduit is configured to be insertable into a mesenteric artery;
    whereby connection of at least one of the inflow and outflow conduits to the vasculature may be made subcutaneously to permit application thereof in a minimally-invasive procedure.

11. A method for increasing perfusion in a branch artery, the method comprising:
    providing fluid communication between a pump and an inflow conduit and between the pump and an outflow conduit;
    fluidly coupling said inflow conduit with a first location of the vasculature using a minimally invasive surgical procedure;
    advancing a distal end of the outflow conduit to a location proximate a branch artery;
    operating said pump to direct blood from the first location to the branch artery at volumetric rates that are on average subcardiac to increase perfusion through the branch artery; and
    advancing the distal end of the outflow conduit into a renal artery.

12. The method of claim 11, further comprising operating the pump in a pulsatile manner.

13. The method of claim 12, further comprising operating the pump at an average flow rate of between about 0.1 and about 3 liters per minute.

14. A method for increasing perfusion in a branch artery, the method comprising:
    providing fluid communication between a pump and an inflow conduit and between the pump and an outflow conduit;
    fluidly coupling said inflow conduit with a first location of the vasculature using a minimally invasive surgical procedure;
    advancing a distal end of the outflow conduit to a location proximate a branch artery;
    operating said pump to direct blood from the first location to the branch artery at volumetric rates that are on average subcardiac to increase perfusion through the branch artery; and
    advancing the distal end of the outflow conduit into a mesenteric artery.

15. The method of claim 14, further comprising operating the pump in a pulsatile manner.

16. The method of claim 14, further comprising operating the pump at an average flow rate of between about 0.1 and about 3 liters per minute.

* * * * *